United States Patent
Van Dyke et al.

(10) Patent No.: US 12,171,758 B1
(45) Date of Patent: Dec. 24, 2024

(54) CRYSTALLINE SALT FORMS OF KAPPA OPIOID RECEPTOR ANTAGONIST AND PRODUCTS AND METHODS RELATED THERETO

(71) Applicant: Neumora Therapeutics, Inc., Watertown, MA (US)

(72) Inventors: Brian Van Dyke, Hightstown, NJ (US); Yawei Shi, Chicago, IL (US); Mengya Ma, Guangdong (CN); Lori Jean Van Orden, San Francisco, CA (US)

(73) Assignee: Neumora Therapeutics, Inc., Watertown, MA (US)

( * ) Notice: Subject to any disclaimer, the term of this patent is extended or adjusted under 35 U.S.C. 154(b) by 0 days.

(21) Appl. No.: 18/764,004

(22) Filed: Jul. 3, 2024

Related U.S. Application Data

(60) Provisional application No. 63/658,791, filed on Jun. 11, 2024, provisional application No. 63/587,966, filed on Oct. 4, 2023, provisional application No. 63/512,040, filed on Jul. 5, 2023.

(51) Int. Cl.
*A61K 31/4709* (2006.01)
*C07D 413/14* (2006.01)

(52) U.S. Cl.
CPC ........ *A61K 31/4709* (2013.01); *C07D 413/14* (2013.01)

(58) Field of Classification Search
CPC .......................... A61K 31/4709; C07D 413/14
USPC .......................................................... 514/313
See application file for complete search history.

(56) References Cited

FOREIGN PATENT DOCUMENTS

WO WO-2018170492 A1 * 9/2018 ......... A61K 31/4709

* cited by examiner

*Primary Examiner* — Kahsay Habte
(74) *Attorney, Agent, or Firm* — Seed IP Law Group LLP

(57) ABSTRACT

Disclosed herein is a solid Form A of 1-(6-ethyl-8-fluoro-4-methyl-3-(3-methyl-1,2,4-oxadiazol-5-yl)quinolin-2-yl)-N-(tetrahydro-2H-pyran-4-yl)piperidin-4-amine hydrochloride exhibiting at least X-ray lines (in degrees 2θ±0.2) at 4.30, 8.59, 12.88, 18.82 and 21.34 in a powder diffraction pattern when measured using Cu Kα radiation. The solid Form A is an antagonist of the kappa-opioid receptor (KOR) and is useful for treating conditions that benefit from the same. Compositions comprising the solid Form A, as well as related methods of use are also disclosed.

30 Claims, 17 Drawing Sheets

CRYSTALLINE SALT FORMS OF KAPPA OPIOID RECEPTOR ANTAGONIST AND PRODUCTS AND METHODS RELATED THERETO

CROSS-REFERENCE TO RELATED APPLICATIONS

This application claims the benefit of priority to U.S. provisional application No. 63/658,791, filed Jun. 11, 2024, and to U.S. provisional application No. 63/587,966, filed Oct. 4, 2023, and to U.S. provisional application No. 63/512,040, filed Jul. 5, 2023, the entire contents of all of which are incorporated herein by reference.

FIELD OF THE INVENTION

The invention relates to a crystalline salt form of a kappa-opioid receptor (KOR) antagonist, to products containing the same, and to methods of their use and preparation.

BACKGROUND

KOR antagonists are recognized for their utility in treating major depression and disorders related to substance abuse or addiction, particularly in the context of rapidly acting treatments which avoid the drawbacks associated with the prototypical KOR antagonists discussed above. Other studies have shown that KOR antagonists may be particularly useful for the treatment of stress-mediated symptoms, as well as for treating social anxiety disorder and phobias. Prophylactic therapy has also been suggested to prevent adverse conditions arising from stress, and in this regard KOR antagonism has been proposed as a preventative treatment of PTSD in individuals at risk of the same. Other therapeutic applications of KOR antagonism include the treatment of impairment in reward-related function as it frequently occurs in patients with mood and anxiety spectrum disorders, and which may also occur with other types of conditions such as schizophrenia or a schizoaffective disorder.

A promising class of KOR antagonists is provided in WO 2018/170492 to Roberts et al. which discloses compounds of the following structure (I):

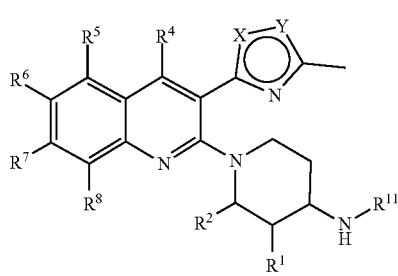

Within the above genus, the following Compound No. 142 (1-(6-ethyl-8-fluoro-4-methyl-3-(3-methyl-1,2,4-oxadiazol-5-yl)quinolin-2-yl)-N-(tetrahydro-2H-pyran-4-yl)-piperidin-4-amine) (also known as Navacaprant, BTRX-335140 or NMRA-335140) has been advanced for clinical development as a selective KOR antagonist in the context of treating neurobehavioral disorders such as major depressive disorder (MDD):

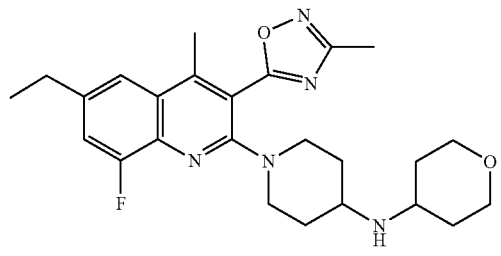

Cpd. No. 142

$$\left(\begin{array}{c}\text{1-(6-ethyl-8-fluoro-4-methyl-3-(3-methyl-1,2,4-oxadiazol-5-yl)}\\ \text{quinolin-2-yl)-N-(tetrahydro-2H-pyran-4-yl)piperidin-4-amine)}\end{array}\right)$$

While significant advances have been made in this field, including the advancement of Compound No. 142 for clinical development, there remains a need for new and/or improved KOR antagonists, as well as for methods related to their use and manufacture, and for pharmaceutical products containing the same.

SUMMARY OF THE INVENTION

In one embodiment, the present invention is directed to a crystalline hydrochloride (HCl) salt of Compound No. 142 (referred to herein as "HCl salt Form A" or "solid Form A") having the following structure:

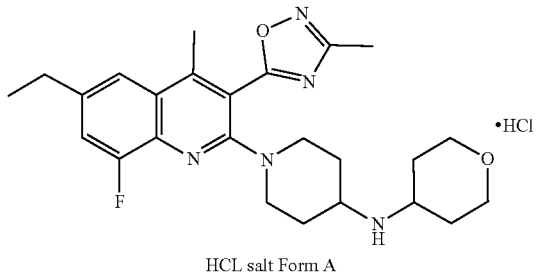 [SMILES: CCc1cc(F)c2nc(N3CCC(NC4CCOCC4)CC3)c(-c3nc(C)no3)c(C)c2c1 ; Cl]

HCL salt Form A

In one embodiment, the HCl salt Form A exhibits at least X-ray lines (in degrees 2θ±0.2) at 4.30, 8.59, 12.88, 18.82 and 21.34 in a powder diffraction pattern when measured using Cu Kα radiation.

In another embodiment, a pharmaceutical composition is provided comprising HCl salt Form A in combination with a pharmaceutically acceptable carrier, diluent or excipient. Such a composition may take the form of, for example, a capsule, tablet, or pill as address in more detail herein below.

In a further embodiment, a method is provided for antagonizing the KOR, the method comprising contacting the receptor with an effective amount of HCl salt Form A, or a pharmaceutical composition comprising the same.

In still a further embodiment, a method is provided for treatment of a malcondition in a subject for which antagonism of the KOR is medically indicated. Such method comprises administering to the subject an effective amount of HCl salt Form A, or a pharmaceutical composition comprising the same, at a frequency and for duration sufficient to provide a beneficial effect to the subject.

DETAILED DESCRIPTION OF THE INVENTION

Figure 1:
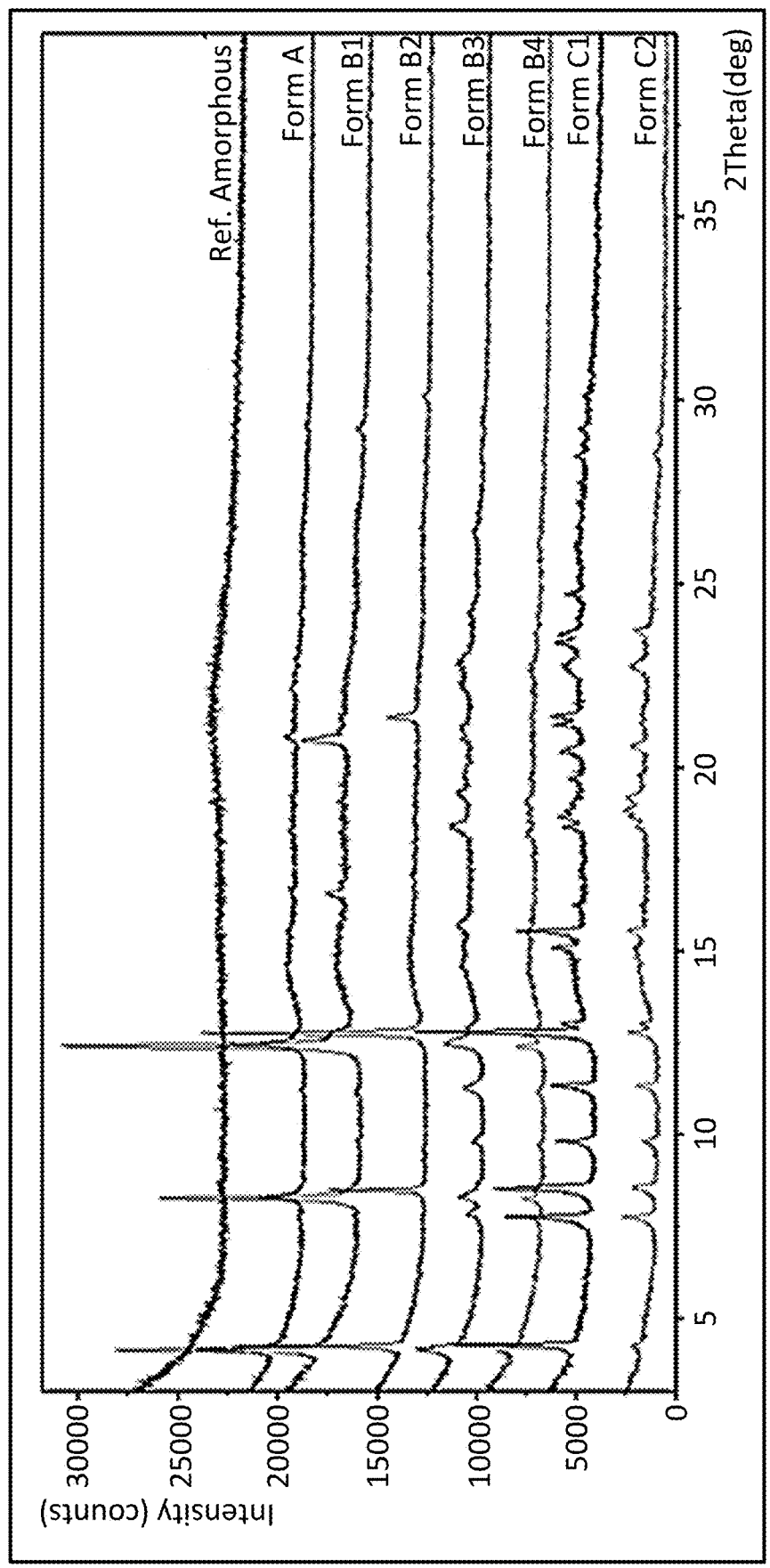
FIG. 1: XRPD overlay of different forms of Compound 142 HCl Salt.

As mentioned above, the invention provides an HCl salt Form A of Compound No. 142 (also referred to herein as "solid Form A" of 1-(6-ethyl-8-fluoro-4-methyl-3-(3-methyl-1,2,4-oxadiazol-5-yl)quinolin-2-yl)-N-(tetrahydro-2H-pyran-4-yl)piperidin-4-amine hydrochloride) having the following structure:

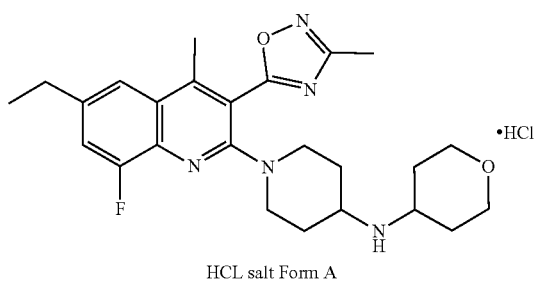 [SMILES: CCc1cc(F)c2nc(N3CCC(NC4CCOCC4)CC3)c(-c3nc(C)no3)c(C)c2c1 ; Cl]

HCL salt Form A

In one embodiment the solid Form A exhibits 1 at least X-ray lines (in degrees 2θ±0.2) at 4.30, 8.59, 12.88, 18.82 and 21.34 in a powder diffraction pattern when measured using Cu Kα radiation.

In another embodiment the solid Form A exhibits at least X-ray lines (in degrees 2θ±0.2) at 4.30, 8.59, 12.88, 18.82 and 21.34, and at least one X-ray line (in degrees 2θ±0.2) selected from the group consisting of 7.83, 9.93, 11.43, 18.55, 22.82 and 29.92, in a powder diffraction pattern when measured using Cu Kα radiation.

In another embodiment the solid Form A exhibits at least X-ray lines (in degrees 2θ±0.2) at 4.30, 8.59, 12.88, 18.82 and 21.34, and at least two X-ray lines (in degrees 2θ±0.2) selected from the group consisting of 7.83, 9.93, 11.43, 18.55, 22.82 and 29.92, in a powder diffraction pattern when measured using Cu Kα radiation.

In another embodiment the solid Form A exhibits at least X-ray lines (in degrees 2θ±0.2) at 4.30, 7.83, 8.59, 9.93, 11.43, 12.88, 18.82, 18.55, 21.34, 22.82 and 29.92 in a powder diffraction pattern when measured using Cu Kα radiation.

In another embodiment the solid Form A exhibits at least X-ray lines (in degrees 2θ±0.2) at 4.30, 7.83, 8.59, 9.93, 11.43, 12.88, 18.82, 18.55, 21.34, 22.82 and 29.92, and at least one X-ray line (in degrees 2θ±0.2) selected from the group consisting of 13.16, 15.08, 15.68, 16.44, 16.84, 17.20, 19.40, 20.84, 23.60, 23.94, 24.91, 27.35, 28.36, 29.18, 30.39, 31.30, 33.50, 34.80, 36.08, 37.83 and 39.32, in a powder diffraction pattern when measured using Cu Kα radiation.

In another embodiment the solid Form A exhibits at least X-ray lines (in degrees 2θ±0.2) at 4.30, 7.83, 8.59, 9.93, 11.43, 12.88, 18.82, 18.55, 21.34, 22.82 and 29.92, and at least two X-ray lines (in degrees 2θ±0.2) selected from the group consisting of 13.16, 15.08, 15.68, 16.44, 16.84, 17.20, 19.40, 20.84, 23.60, 23.94, 24.91, 27.35, 28.36, 29.18, 30.39, 31.30, 33.50, 34.80, 36.08, 37.83 and 39.32, in a powder diffraction pattern when measured using Cu Kα radiation.

In another embodiment the solid Form A exhibits at least X-ray lines (in degrees 2θ±0.2) at 4.30, 7.83, 8.59, 9.93, 11.43, 12.88, 18.82, 18.55, 21.34, 22.82 and 29.92, and at least three X-ray lines (in degrees 2θ±0.2) selected from the group consisting of 13.16, 15.08, 15.68, 16.44, 16.84, 17.20, 19.40, 20.84, 23.60, 23.94, 24.91, 27.35, 28.36, 29.18, 30.39, 31.30, 33.50, 34.80, 36.08, 37.83 and 39.32, in a powder diffraction pattern when measured using Cu Kα radiation.

In another embodiment the solid Form A exhibits at least X-ray lines (in degrees 2θ±0.2) at 4.30, 7.83, 8.59, 9.93, 11.43, 12.88, 13.16, 15.08, 15.68, 16.44, 16.84, 17.20, 18.82, 18.55, 19.40, 20.84, 21.34, 22.82, 23.60, 23.94, 24.91, 27.35, 28.36, 29.18, 29.92, 30.39, 31.30, 33.50, 34.80, 36.08, 37.83 and 39.32 in a powder diffraction pattern when measured using Cu Kα radiation.

In another embodiment the solid Form A exhibits at least X-ray lines at the same angles (in degrees 2θ±0.2) shown in Table 1 below in a powder diffraction pattern when measured using Cu Kα radiation.

Figure 13:
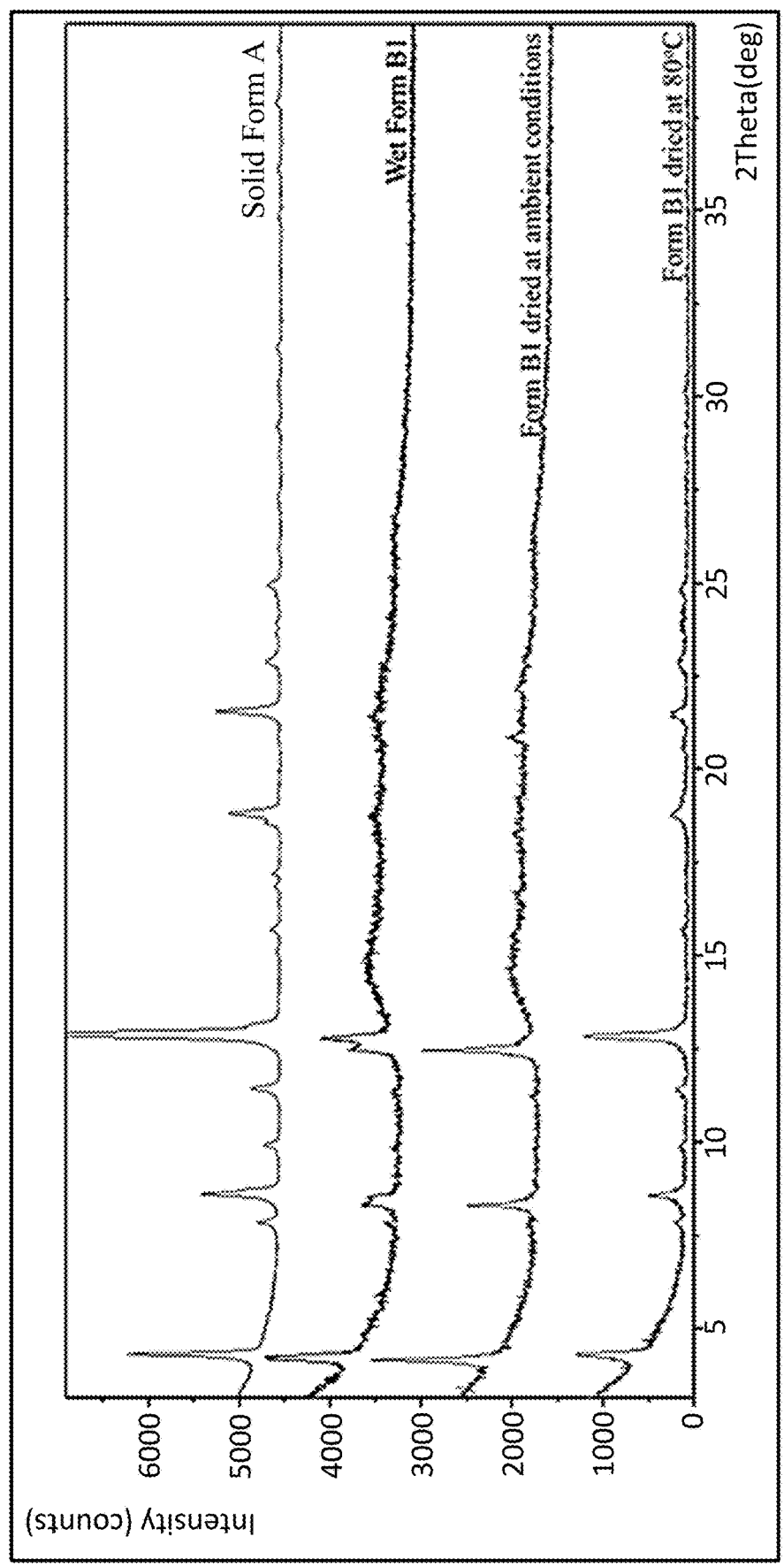
FIG. 13: XRPD overlay of wet, solvated and desolvated forms B1 of Compound 142 HCl salt in comparison to the solid Form A of Compound 142 HCl salt.

In another embodiment the solid Form A exhibits an X-ray pattern essentially the same as that provided in FIG. 13 in a powder diffraction pattern when measured using Cu Kα radiation.

TABLE 1

Tabulated XRPD peak data of the Solid Form A of 1-(6-ethyl-8-fluoro-4-methyl-3-(3-methyl-1,2,4-oxadiazol-5-yl)quinolin-2-yl)-N-(tetrahydro-2H-pyran-4-yl) piperidin-4-amine hydrochloride in a powder diffraction pattern when measured using Cu Kα radiation.
Solid Form A

| Peak | X-ray lines (in degrees 2θ ± 0.2) |
|---|---|
| 1 | 4.30 |
| 2 | 7.83 |

TABLE 1-continued

Tabulated XRPD peak data of the Solid Form A of
1-(6-ethyl-8-fluoro-4-methyl-3-(3-methyl-1,2,4-oxadiazol-5-
yl)quinolin-2-yl)-N-(tetrahydro-2H-pyran-4-yl) piperidin-4-amine
hydrochloride in a powder diffraction pattern when measured
using Cu Kα radiation.
Solid Form A

| Peak | X-ray lines (in degrees 2θ ± 0.2) |
|---|---|
| 3 | 8.59 |
| 4 | 9.93 |
| 5 | 11.43 |
| 6 | 12.88 |
| 7 | 13.16 |
| 8 | 15.08 |
| 9 | 15.68 |
| 10 | 16.44 |
| 11 | 16.84 |
| 12 | 17.20 |
| 13 | 18.55 |
| 14 | 18.82 |
| 15 | 19.40 |
| 16 | 20.84 |
| 17 | 21.54 |
| 18 | 22.8 |
| 19 | 23.60 |
| 20 | 23.94 |
| 21 | 24.91 |
| 22 | 25.92 |
| 23 | 27.35 |
| 24 | 28.36 |
| 25 | 29.18 |
| 26 | 30.39 |
| 27 | 31.30 |
| 28 | 33.50 |
| 29 | 34.80 |
| 30 | 36.08 |
| 31 | 37.83 |
| 32 | 39.32 |

In another embodiment the solid Form A exhibits the X-ray lines at the same angles (in degrees 2θ±0.2) shown in Table 1 and is substantially free of additional X-ray lines not included in Table 1 in a powder diffraction pattern when measured using Cu Kα radiation.

In another embodiment the solid Form A exhibits an X-ray pattern that is substantially free of X-ray lines (in degrees 2θ 0.2) at 3.1, 19.1, 20.0, 20.5, 21.2, 24.3, 25.3, 29.9 and 35.5.

In another embodiments the solid Form A exhibits an X-ray pattern that is substantially free of X-ray lines (in degrees 2θ±0.2) at 3.1, 9.7, 11.2, 12.6, 15.4, 16.2, 19.1, 20.0, 20.5, 21.2, 21.8, 24.3, 24.6, 25.3, 29.9 and 35.5.

In certain embodiments, the disclosure provides pharmaceutical compositions comprising the HCl salt Form A of Compound No. 142 together with at least one pharmaceutically acceptable carrier, diluent or excipient.

For example, the solid Form A will usually be mixed with a carrier, or diluted by a carrier, or enclosed within a carrier which can be in the form of an ampoule, capsule, sachet, paper, or other container. When the solid Form A is mixed with a carrier, or when the carrier serves as a diluent, it can be solid, semi-solid, or liquid material that acts as a vehicle, excipient, or medium for the active compound.

The solid Form A can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

For parenteral administration, the carrier will typically comprise sterile water, although other ingredients that aid solubility or serve as preservatives can also be included. Furthermore, injectable suspensions can also be prepared, in which case appropriate liquid carriers, suspending agents and the like can be employed.

For topical administration, the compounds of the present invention can be formulated using bland, moisturizing bases such as ointments or creams.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent. Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The solid Form A can be formulated for parenteral administration by injection such as by bolus injection or continuous infusion. A unit dosage form for injection can be in ampoules or in multi-dose containers.

The formulations of the invention can be designed to provide quick, sustained, or delayed release of the solid Form A after administration to the patient by employing procedures well known in the art. Thus, the formulations can also be formulated for controlled release or for slow release. Compositions of the present disclosure can include, for example, micelles or liposomes, or some other encapsulated form, or can be administered in an extended-release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain the solid Form A, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the solid Form A dissolved in polyhydroxylated castor oil.

Dosage forms can be administered once a day, or more than once a day, such as twice or thrice daily. Alternatively, dosage forms can be administered less frequently than daily, such as every other day, or weekly, if found to be advisable by a prescribing physician. Dosing regimens include, for example, dose titration to the extent necessary or useful for the indication to be treated, thus allowing the patient's body to adapt to the treatment and/or to minimize or avoid unwanted side effects associated with the treatment. Other dosage forms include delayed or controlled-release forms. Suitable dosage regimens and/or forms include those set out, for example, in the latest edition of the Physicians' Desk Reference, incorporated herein by reference.

When used to prevent the onset disease or condition, the solid Form A can be administered to a subject at risk for developing the condition, typically on the advice and under the supervision of a physician, at the dosage levels described above. Subjects at risk for developing a particular disease or condition generally include those that have a family history of the same, or those who have been identified by genetic testing or screening to be particularly susceptible to developing the disease or condition.

Chronic administration refers to administration of the solid Form A or pharmaceutical compositions thereof over an extended period of time, e.g., for example, over 3 months, 6 months, 1 year, 2 years, 3 years, 5 years, etc., or may be continued indefinitely, for example, for the rest of the subject's life. In certain embodiments, the chronic administration is intended to provide a constant level of Compound 142 in the blood, e.g., within the therapeutic window over the extended period of time.

In another embodiment, there are provided methods of making a composition of the solid Form A including formulating the solid Form A with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

In another embodiment, a method is provided for antagonizing the KOR, the method comprising contacting the receptor with an effective amount of HCl salt Form A, or a pharmaceutical composition comprising the same.

As used herein, "KOR" and "OPRK1" refer to the kappa-opioid receptor (KOR) that is encoded by the OPRK1 gene ("KOR" and "OPRK1" are used interchangeably herein). Similarly, "DOR" and "OPRD" refer to the delta-opioid receptor (DOR) that is encoded by the OPRD gene ("DOR" and "OPRD" are used interchangeably herein), and "MOR" and "OPRM1" refer to the mu-opioid receptor (MOR) that is encoded by the OPRM1 gene ("MOR" and "OPRM1" are used interchangeably herein).

The term "antagonism" is used herein to encompass molecules that interact in some way with a receptor and thereby function as an antagonist, either by binding to the receptor at the binding site of its natural ligand or at locations other than the binding site. The "kappa opioid receptor" or "KOR" is a member of the opioid receptor family which binds the opioid peptide dynorphin as the primary endogenous ligand. The phrase to "KOR antagonism" used herein to encompass molecules that interact in some way with KOR and thereby function as an antagonist, either by binding to KOR at the site of dynorphin, or at a location other than the binding site (i.e., allosteric binding).

In an embodiment, a method is provided for treatment of a neuropsychiatric or behavioral condition, whether organic, stress-induced or iatrogenic, that is characterized by elevations in serum prolactin and respond to KOR antagonist administration with a reduction in serum prolactin. Such method comprises administering to the subject an effective amount of HCl salt Form A, or a pharmaceutical composition comprising the same, at a frequency and for duration sufficient to provide a beneficial effect to the subject.

In a further embodiment, a method is provided for treatment of a malcondition in a subject for which antagonism of the KOR is medically indicated. Such method comprises administering to the subject an effective amount of HCl salt Form A, or a pharmaceutical composition comprising the same, at a frequency and for duration sufficient to provide a beneficial effect to the subject.

As used herein, a "subject" means both mammals and non-mammals. Mammals include, for example, humans; non-human primates, e.g., apes and monkeys; cattle; horses; sheep; and goats. Non-mammals include, for example, fish and birds.

"Treating" or "treatment" within the meaning herein refers to an alleviation of symptoms associated with a disorder or disease, or inhibition of further progression or worsening of those symptoms, or prevention or prophylaxis of the disease or disorder in certain conditions.

The expression "effective amount", when used to describe use of a compound of the invention in providing therapy to a subject suffering from a disorder or malcondition mediated by KOR refers to the amount of a compound of the invention that is effective to bind to as an antagonist the KOR in the individual's tissues, wherein the KOR is implicated in the disorder, wherein such binding occurs to an extent sufficient to produce a beneficial therapeutic effect on the subject.

As used herein, the phase "essentially the same" means that the X-ray line angles of an X-ray pattern may individually vary by a percentage as low as 5% below the value illustrated in the described X-ray pattern, or may individually vary by a percentage as high as 5% above the value illustrated in the described X-ray pattern. In some embodiments, the phase "essentially the same" means that the X-ray line angles of an X-ray pattern may individually vary by a percentage as low as 4% below the value illustrated in the described X-ray pattern, or may individually vary by a percentage as high as 4% above the value illustrated in the described X-ray pattern. In some embodiments, the phase "essentially the same" means that the X-ray line angles of an X-ray pattern may individually vary by a percentage as low as 3% below the value illustrated in the described X-ray pattern, or may individually vary by a percentage as high as 3% above the value illustrated in the described X-ray pattern. In some embodiments, the phase "essentially the same" means that the X-ray line angles of an X-ray pattern may individually vary by a percentage as low as 2% below the value illustrated in the described X-ray pattern, or may individually vary by a percentage 30 as high as 2% above the value illustrated in the described X-ray pattern. In some embodiments, the phase "essentially the same" means that the X-ray line angles of an X-ray pattern may individually vary by a percentage as low as 1% below the value illustrated in the described X-ray pattern, or may individually vary by a percentage as high as 1% above the value illustrated in the described X-ray pattern.

As used herein, the phase "substantially free" means that the powder diffraction pattern does not show an X-ray line with an amplitude that exceeds a magnitude of noise in the baseline of the powder diffraction pattern.

The term "malcondition" is used to describe any disease, disorder or condition, and are used interchangeably, and in the context of this application refers to a disease, disorder or condition wherein KOR plays a role in the biochemical mechanisms involved in the malcondition, or symptoms thereof, such that a therapeutically beneficial effect can be achieved by acting on such KOR.

In certain embodiments, the present invention provides a method for antagonizing a KOR with a compound of the invention. The method involves contacting the receptor with a suitable concentration of Compound 142 to antagonize the receptor. The contacting can take place in vitro, for example in carrying out an assay to determine the KOR inhibition activity of the solid Form A undergoing experimentation related to a submission for regulatory approval.

In certain embodiments, the method for antagonizing a KOR can also be carried out in vivo, that is, within the living body of a mammal, such as a human patient or a test animal (referred to as a "subject" herein). The solid Form A can be supplied to the living organism via one of the routes as described above, e.g., orally, or can be provided locally within the body tissues. In the presence of the solid Form A, inhibition of the receptor takes place, and the effect thereof can be studied.

Methods of treatments provided by the invention include administration of the solid Form A, alone or in combination with another pharmacologically active agent or second medicament to a subject or patient having a malcondition for which antagonizing the KOR is medically indicated, such as: an addictive disorder, including disorders related to substance abuse or addiction; CNS-related disorders; anxiety disorders; depressive disorders; mood disorders; schizophrenia or schizoaffective disorders; stress-related disorders; obesity and eating disorder; migraine; postnatal depression; neurodegenerative diseases and disorders, including disorders of mood and behavior associated with neurodegenerative diseases; postnatal depression; anesthesia and/or sedation; epilepsy; status epilepticus; and seizure.

In an embodiment, a method is provided for treatment of an addictive disorder, including a disorders related to substance abuse or addiction, and compulsive behavior, comprising administering to a subject in need thereof an effective amount of the solid Form A, or a pharmaceutical composition comprising the same, at a frequency and for a duration sufficient to provide a beneficial effect to the subject.

Disorders related to substance abuse or addiction as described herein can include gambling, drug addiction, drug abuse, alcohol dependence, alcohol abuse, substance-induced depression and mood disorders induced by substances such as alcohol, nicotine, amphetamine, methamphetamine, cocaine, opiate addiction, heroin addiction, benzodiazepines and the like.

In an embodiment, a method is provided for treatment of CNS-related disorder, comprising administering to a subject in need thereof an effective amount of the solid Form A, or a pharmaceutical composition comprising the same, at a frequency and for a duration sufficient to provide a beneficial effect to the subject.

CNS-related disorders include substance abuse related disorders and/or withdrawal syndromes, mood disorders, anxiety disorders, schizophrenia spectrum disorders, pain, personality disorders, autism spectrum disorders, eating disorder; sleep disorder; disorders of memory and/or cognition, head shock and traumatic brain injury; vascular diseases and cognitive disorders.

Exemplary CNS conditions include substance abuse disorders and/or withdrawal syndromes (including addiction to opiates, cocaine, and/or alcohol); mood disorders (including depression, dysthymic disorder, bipolar disorder); anxiety disorders and including compulsive disorders such as obsessive-compulsive disorder (OCD), social phobia, generalized anxiety disorder (GAD), social anxiety disorder; stress, post-traumatic stress disorder (PTSD); schizophrenia spectrum disorders (including schizophrenia, schizoaffective disorder); pain (including migraine, neuropathic pain, injury related pain syndromes, acute pain, chronic pain); personality disorders (including anti-social personality disorder, obsessive compulsive personality disorder); autism spectrum disorders (ASD) (including autism, monogenetic causes of autism such as synaptopathies, e.g., Rett syndrome, Fragile X syndrome, Angelman syndrome); eating disorders; sleep disorders (including insomnia); disorders of memory and/or cognition (including attention disorders (e.g., attention deficit hyperactivity disorder (ADHD)), dementia (including Alzheimer's type dementia, Lewis body type dementia, vascular type dementia), head shock and traumatic brain injury (TBI); vascular diseases (including stroke, ischemia, vascular malformations) and cognitive disorders (including Alzheimer's disease and other forms of dementia).

In an embodiment, a method is provided for treatment of an anxiety disorder, comprising administering to a subject in need thereof an effective amount of the solid Form A, or a pharmaceutical composition comprising the same, at a frequency and for a duration sufficient to provide a beneficial effect to the subject.

Anxiety disorder is a blanket term covering several different forms of abnormal and pathological fear and anxiety. Current psychiatric diagnostic criteria recognize a wide variety of anxiety disorders, including generalized anxiety disorder, panic disorder, stress-related disorders, obsessive compulsive disorder, phobia, social anxiety disorder, separation anxiety disorder and post-traumatic stress disorder (PTSD). In one embodiment, the anxiety disorder is a social anxiety disorder. In one embodiment, the anxiety disorder is phobia. In one embodiment, the anxiety disorder is a stress-related disorder. In one embodiment, the anxiety related disorder is PTSD.

Generalized anxiety disorder is a common chronic disorder characterized by long-lasting anxiety that is not focused on any one object or situation. A person suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attack's potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life-threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of Phobia, which includes all cases in which fear and anxiety is triggered by a specific stimulus or situation. Sufferers typically anticipate terrifying consequences from encountering the object of their fear, which can be anything from social phobia, specific phobia, agoraphobia, phobia of an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

In an embodiment, a method is provided for treatment of a depressive disorder, depression, or depressive illness, comprising administering to a subject in need thereof an effective amount of the solid Form A, or a pharmaceutical composition comprising the same, at a frequency and for duration sufficient to provide a beneficial effect to the subject. Examples of such disorders include major depression, drug-resistant depression, dysthymia and bipolar disorder.

In an embodiment, a method is provided for treatment of a mood disorder, or an affective disorder comprising administering to a subject in need thereof an effective amount of the solid Form A, or a pharmaceutical composition comprising the same, at a frequency and for duration sufficient to provide a beneficial effect to the subject.

Examples of a mood disorder or a affective disorder include major depressive disorder (MDD); bipolar disorder; anhedonia; dysthymia; major depression, Psychotic major depression (PMD), or psychotic depression; postpartum depression; seasonal affective disorder (SAD); and catatonic depression is a rare and severe form of major depression involving disturbances of motor behavior and other symptoms The terms "anhedonia" and "anhedonic symptom" are used interchangeably and is defined as the inability to experience pleasure from activities usually found enjoyable, e.g. exercise, hobbies, music, sexual activities or social interactions. The terms "anhedonia" and "anhedonic symptom" are closely related to criterion of "depressive disorder with melancholic features" which is defined in DSM-5 as melancholic depression characterized by a loss of pleasure in most or all activities, a failure of reactivity to pleasurable stimuli, a quality of depressed mood more pronounced than that of grief or loss, a worsening of symptoms in the morning hours, early morning waking, psychomotor retardation, excessive weight loss, or excessive guilt. The term "treatment of depressive disorder with melancholic features" comprises treatment of both the depressive disorder and melancholic features associated herewith. In one embodiment, the mood disorder is anhedonia. In one embodiment, the mood disorder is major depression. In one embodiment, the mood disorder is seasonal affective disorder (SAD).

In other embodiments, a method is provided for treatment of a schizophrenia or a schizoaffective disorder, comprising administering to a subject in need thereof an effective amount of the solid Form A, or a pharmaceutical composition comprising the same, at a frequency and for duration sufficient to provide a beneficial effect to the subject.

In other embodiments, a method is provided for treatment of obesity or an eating disorder, comprising administering to a subject in need thereof an effective amount of the solid Form A, or a pharmaceutical composition comprising the same, at a frequency and for duration sufficient to provide a beneficial effect to the subject. Obesity and eating disorders as described here can include bulimia, anorexia nervosa, and the like.

In other embodiments, a method is provided for treatment of migraine, comprising administering to a subject in need thereof an effective amount of the solid Form A, or a pharmaceutical composition comprising the same, at a frequency and for duration sufficient to provide a beneficial effect to the subject. In another embodiment, prophylactic therapy is provided to prevent migraine. In this regard KOR antagonism is proposed as a preventative treatment of migraine in individuals at risk of the same.

In an embodiment, a method is provided for treatment of postnatal depression, comprising administering to a subject in need thereof an effective amount of the solid Form A, or a pharmaceutical composition comprising the same, at a frequency and for a duration sufficient to provide a beneficial effect to the subject.

Immediately after birth, progesterone levels decrease dramatically leading to the onset of postnatal depression (PND). The symptoms of PND range from mild depression to psychosis requiring hospitalization. PND is also associated with severe anxiety and irritability. PND-associated depression is not amenable to treatment by classic antidepressants, and women experiencing PND show an increased incidence of premenstrual syndrome (PMS).

The invention is further illustrated by the following Example, which is intended to be non-limiting and representative of various aspects of the invention.

EXAMPLES

A. Abbreviations

ACN Acetonitrile
DCM Dichloromethane
DMSO Dimethylsulfoxide
DSC Differential scanning calorimetry
EtOAc Ethyl acetate
EtOH Ethanol
HPLC High-performance liquid chromatography
IPA Isopropyl alcohol
MEC Molar extinction coefficient
MeOH Methanol
PTFE Polytetrafluoroethylene
RT Room temperature
SD standard deviation
TGA Thermogravimetric analysis
XRPD X-ray powder diffraction B. Instruments and Methods XRPD Method 1

XRPD patterns were detected with PANalytical XRPD instruments. The solid sample was spread on a zero-background Si sample holder. The XRPD parameters used in XRPD Method 1 are listed in Table 2.

TABLE 2

Parameters for XRPD Method 1

| Parameters | X' Pert3 |
| --- | --- |
| X-Ray wavelength | Cu, kα, K$\alpha$1 (Å): 1.540598, K$\alpha$2 (Å): 1.544426 K$\alpha$2/K$\alpha$1 intensity ratio: 0.50 |
| X-Ray tube setting | 43 kV, 40 mA |
| Divergence slit | 1/8° |
| Scan mode | Continuous |
| Scan range (° 2TH) | 3°-40° |
| Step size (° 2TH) | 0.0263 |
| Scan step time (s) | 50 |
| Test time(s) | ~5 min 04 s |

XRPD Method 2

XRPD was also performed with a Panalytical X'Pert Powder XRPD on a Si zero-background holder. The 2θ position was calibrated against a Panalytical Si reference standard disc. All wet-cake diffractograms were collected with the sample under Kapton film. The parameters used in XRPD Method 2 are listed in Table 3.

TABLE 3

Parameters for XRPD Method 2

| Parameters | Reflection Mode |
| --- | --- |
| X-Ray wavelength | Cu, kα K$\alpha$1 (Å): 1.540598, K$\alpha$2 (Å): 1.544426, K$\alpha$2/K$\alpha$1 intensity ratio: 0.50 |
| X-Ray tube setting | 45 kV, 40 mA |
| Divergence slit | Fixed 1/8° |
| Scan mode | Continuous |
| Scan range (° 2TH) | 3-40 |

TABLE 3-continued

Parameters for XRPD Method 2

| Parameters | Reflection Mode |
| --- | --- |
| Scan step time [s] | 18.87 |
| Step size (° 2TH) | 0.0131 |
| Test Time | 4 min 15 s |

XRPD Peaks were tabulated from fittings generated in X'pert HighScore Plus for greatest accuracy. Each XRPD pattern disclosed herein was baseline corrected, then fitted to the peaks.

The threshold for considering a peak to be unique from Form A was a difference of >±0.1° for all peak positions.

TGA and DSC Measurements

TGA data were obtained using a TA Q5000 TGA from TA Instruments and DSC was performed using a TA Q2000 DSC from TA Instruments. Detailed parameters used are listed in Table 4.

TABLE 4

Parameters for TGA and DSC Measurements

| Parameters | TGA | DSC |
| --- | --- | --- |
| Method | Ramp | Ramp |
| Sample pan | Aluminum, open | Aluminum, crimped |
| Temperature | RT-desired temperature | 25° C.-desired temperature |
| Heating rate | 10° C./min | 10° C./min |
| Purge gas | $N_2$ | $N_2$ |

HPLC Analyses

HPLC analyses were performing using an Agilent 1260 HPLC, and detailed chromatographic conditions for purity and solubility measurements are listed in Table 5.

TABLE 5

HPLC conditions and parameters

| Parameters | Value | | | |
| --- | --- | --- | --- | --- |
| HPLC | Agilent 1260 VWD detector | | | |
| Column | YMC-Triart C18, 4.6 mm × 150 mm, 3 μm | | | |
| Mobile phase | A: 0.1% TFA in $H_2O$ B: 0.1% TEA in ACN | | | |
| | Purity | | Solubility | |
| Gradient table | Time (min) | % B | Time (min) | % B |
| | 0.0 | 10 | 0.0 | 10 |
| | 15.0 | 60 | 6.0 | 90 |
| | 20.0 | 90 | 7.0 | 10 |
| | 21.0 | 10 | 10.0 | 10 |
| | 25.0 | 10 | / | / |
| Run time | 25.0 min | | 10.0 min | |
| Post time | 0.0 min | | | |
| Flow rate | 1.0 mL/min | | | |
| Parameters | Value | | | |
| Injection volume | 5 μL | | | |
| Detector wavelength | UV at 268 nm | | | |
| Column temperature | 35° C. | | | |
| Sample temperature | RT | | | |
| Diluent | ACN:$H_2O$ (1:1, v/v) | | | | pKa Measurements pKa measurements were taken using a Sirius T3 instrument in a solvent (MeOH and KCl solution). The process ran from low to high pH (2 to 12).

MEC Measurements

Approximately 3.0 mg of HCl salt of Compound No. 142 was weighed into a 10-mL volumetric flask. The actual weight was recorded. The solid was dissolved and diluted to volume with ACN:H$_2$O (1:1, v/v). Stock solutions were prepared in duplicate. The stock solutions were diluted by 50 times by transferring 1 mL of stock solution into 50-mL volumetric flask and then diluted to volume with ACN/water ACN:H$_2$O (1:1, v/v). The ⅟₅₀ solutions were used to collect spectra with full wave scanning from 190 nm to 700 nm and absorbance at 235 nm, 270 nm, 290 nm and 365 nm using spectrophotometer with the background subtracted. MEC was then calculated by the following equation:

$$MEC(L\ mol-1\ cm-1) = Absorbance/conc.(mol/L)/Cell\ length(cm)$$

Log D7.6 Measurements

Preparation of Solvents 0.1 M KH$_2$PO$_4$: 1.36 g of solid KH$_2$PO$_4$ was added into a 100-mL volumetric flask, the solid was dissolved with ultrapure water and diluted to volume.

0.1 M K$_2$HPO$_4$: 1.73 g of solid K$_2$HPO$_4$ was added into a 100-mL volumetric flask, the solid was dissolved with ultrapure water and diluted to volume.

100 mL of 0.1 M K$_2$HPO$_4$ solution and 30 mL of 0.1 M KH$_2$PO$_4$ was transferred to a 250-mL beaker and mixed. Then, pH was adjusted 7.4 with the KH$_2$PO$_4$ solution.

Octanol and aqueous buffer were pre-equilibrated by adding 10 mL octanol and 10 mL aqueous buffer into a 20-mL glass vial and agitating the vial for 24 hrs. The mutually saturated octanol and aqueous buffer were then separated after phase separation.

Sample Set up

Approximately 1.0 mg solids were weighted into a 3-mL glass vial with 1.0 mL of octanol inside, and dissolution was accelerated by ultrasonication. Then, 1.0 mL of complementary aqueous buffer was added into the vial. Samples were prepared in triplicate. The glass vial was sealed and mixed on a rotary mixer at 25° C. for 24 hrs.

Sample Analysis and Data Calculation

After phase separated, the phases were physically separated, and the concentrations of compounds in each phase were determined by HPLC using the HPLC conditions and parameters in Table 5.

Distribution coefficient, referred to as $D_{ow}$, was calculated as the concentration of the test compound (both ionized and unionized) in the octanol phase divided by the corresponding concentration in the aqueous phase. Log $D_{7.6}$ was calculated as an average of the log 10 of $D_{ow}$ based on three runs.

Solubility/Stability Measurements in pH Buffers

Stock Solution Preparation 0.2 M Hydrochloric Acid: 166 µL of 12 M hydrochloric acid is added into a 10-mL volumetric flask, and the resulting mixture was diluted to volume with purified water and mixed.

0.2 M Sodium Hydroxide: 80.0 mg of sodium hydroxide was weighted into a 10-mL volumetric flask. The solid was dissolved with volume of purified water, diluted to volume and mixed.

0.2 M Potassium Chloride: 148.8 mg of potassium chloride was weighted into a 10-mL volumetric flask. The solid was dissolved with volume of purified water, diluted to volume and mixed.

0.2 M Potassium Phosphate, Monobasic: 271.5 mg of monobasic potassium phosphate (KH2PO4) was weighed into a 10-mL volumetric flask. The solid was dissolved with appropriate volume of purified water, diluted to volume and mixed.

0.2 M Boric Acid and Potassium Chloride: 124.3 mg of boric acid (H3BO3) and 149.5 mg of potassium chloride (KCl) were mixed into a 10-mL volumetric flask. The solid was dissolved with appropriate volume of purified water, diluted to volume and mixed.

pH Buffers Preparation 50 mM KCl pH 2.0 buffer: 2.5 mL of 0.2 M potassium chloride solution and 0.65 mL of 0.2 M hydrochloric acid solution were transferred to a 10-mL volumetric flask. Purified water is added to the target volume, and pH is adjusted to 2.0. The mixture was then diluted to volume with purified water, mixed, and pH was measured with a pH meter.

50 mM citrate pH 4.0 buffer: 65.3 mg of citric acid (monohydrate) and 56.9 mg of sodium citrate (dihydrate) were transferred to a 10-mL volumetric flask, purified water was added to obtain the target volume, and pH was adjust to 4.0. The mixture was then diluted to volume with purified water, mixed, and pH was checked with a pH meter.

50 mM phosphate pH 6.0 buffer: 2.5 mL of 0.2 M monobasic potassium phosphate solution and 0.28 mL of 0.2 M sodium hydroxide solution were transferred to a 10-mL volumetric flask, purified water was added to obtain the target volume, and pH was adjusted 6.0. The mixture was diluted to volume with purified water, mixed, and pH was checked using a pH meter.

50 mM phosphate pH 8.0 buffer: 2.5 mL of 0.2 M monobasic potassium phosphate solution and 2.31 mL of 0.2 M NaOH solution were transferred into a 10-mL volumetric flask, purified water was added to obtain the target volume, and pH was adjusted to 8.0. The mixture was diluted to volume with purified water, mixed, and pH was checked using a pH meter.

50 mM borate pH 10.0 buffer: 2.5 mL of 0.2 M boric acid and potassium chloride solution and 2.2 mL of 0.2 M NaOH solution were transferred into a 10-mL volumetric flask, purified water was added to obtain the target volume, and pH was adjusted to 10.0. The mixture was diluted to volume with purified water, mixed, and pH was checked using a pH meter.

Analyses of Solubility and Stability using HPLC

Approximately 12 mg of material to be analyzed was transferred into 2-mL glass vial, and 1.2 mL of corresponding solvent was added to form a suspension (solid loading: 10 mg/mL).

Magnetic stirring is maintained at 25° C. for 24 hrs.

The resulting suspension is centrifuged, and the supernatant is filtered through a 0.22 µm PTFE membrane.

Solubility and purity were measured using the conditions and parameters in Table 5, and pH of supernatant was measured as described above.

HPLC purity of suspension was measured by transferring 0.05 mL of suspension and dissolving in 0.95 mL of ACN/H2O, (1:1, v/v) and performing HPLC analysis using the conditions and parameters of Table 5.

Solubility Measurement in Organic Solvents 15-65 mg of material to be analyzed was weighted into a 2-mL glass vial and 1.2 mL of respective solvent was added to form a suspension.

magnetic stirring at 25° C. was maintained for 24 hrs.

The resulting suspension was centrifuged and the supernatant was filtered through a 0.22 µm PTFE membrane.

Solubility was measured using the conditions and parameters in Table 5.

C. Preparation and Characterization of Solvate Forms of Compound 142 HCl Salt

Example 1: Preparation of Compound 142 HCl Salt as Amorphous Solid

The free base of Compound 142 was prepared as described at pages 170-174 of Roberts et al. (WO 2018/170492), and the free base was then converted into a hydrochloride salt by combination with dilute hydrochloric acid in DCM followed by evaporation to obtain the HCl salt of Compound 142 as an amorphous solid. The Compound 142 HCl salt was converted to an amorphous solid by planetary ball-milling at 600 rpm for 90 min.

Example 2: Solvent Screen of Compound 142 HCl Salt

Solvent screening experiments were carried out using the amorphous Compound 142 HCl Salt of Example 1. These experiments included temperature cycling, slow cooling, slow evaporation, liquid vapor diffusion and slurry conversions at 5° C. using a variety of solvent combinations. Solid forms obtained from these experiments were dried at temperatures up to 60°

TABLE 6

Summary of forms obtained from solvate screen

| Type | Solidification Conditions | Morphology (PLM) | Solvent (GC) |
|---|---|---|---|
| A | Slow-cooling in 3:1:8 ACN:H$_2$O:EtOAc | Birefringent Needles | EtOAc |
| B1 | Liquid vapor diffusion in DCM/pentane | Irregular, Birefringent particles | N/A |
| B2 | Liquid vapor diffusion in EtOH/pentane | Rod-shaped Birefringent particles | N/A |
| B3 | Liquid vapor diffusion in DCM/toluene | Irregular, Birefringent particles | DCM |
| B4 | Temperature cycling in DCM | Irregular, Birefringent particles | DCM |
| C1 | 5° C. slurry in ACN | Small Birefringent needle-like particles | No solvent |
| C2 | 5° C. slurry in H$_2$O | Birefringent Needles/Irregular particles | Acetone (C2 from Temp. Cycling in Acetone) |

XRPD analyses were carried out on the HCl salt Types A, B1, B2, B3, B4, C1 and C2 using the XRPD Method 1 described above by reference to Table 2. FIG. 1 shows an XRPD overlay of these HCl salts in comparison to the amorphous solid of Example 1.

Example 3: Characterization of HCl Salt Type A

Ex. 3-1: XRPD of HCl Salt Type A

Figure 2:
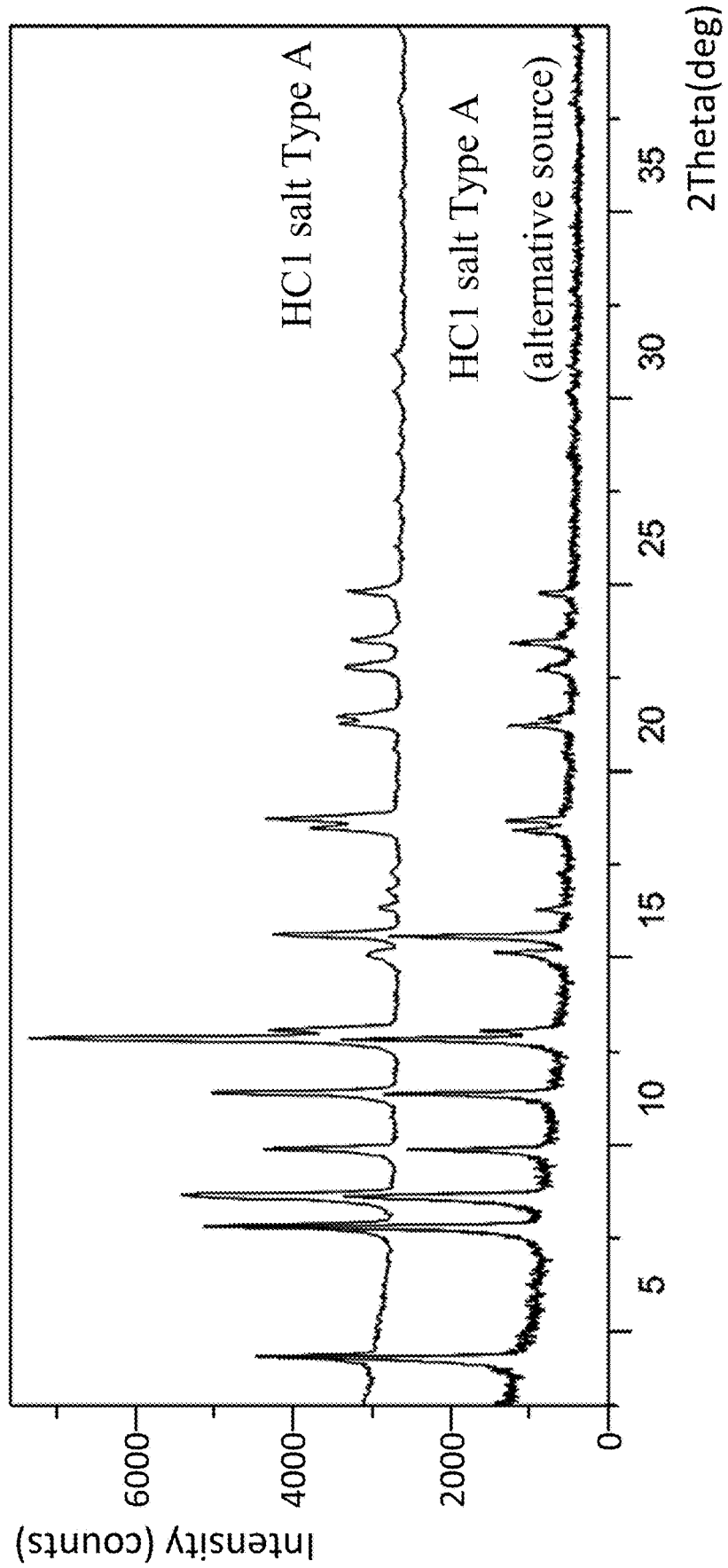
FIG. 2: XRPD overlay of two batches of the HCl salt type A.

Additional batches of the HCl salt Type A were prepared, and XRPD analyses were carried out on two batches of the HCl salt Type A using the XRPD Method 1 described above with reference to Table 2. FIG. 2 shows an XRPD overlay of the two batches of the HCl salt Type A.

Ex. 3-2: TGA/DSC Analyses of HCl Salt Type A

Figure 3:
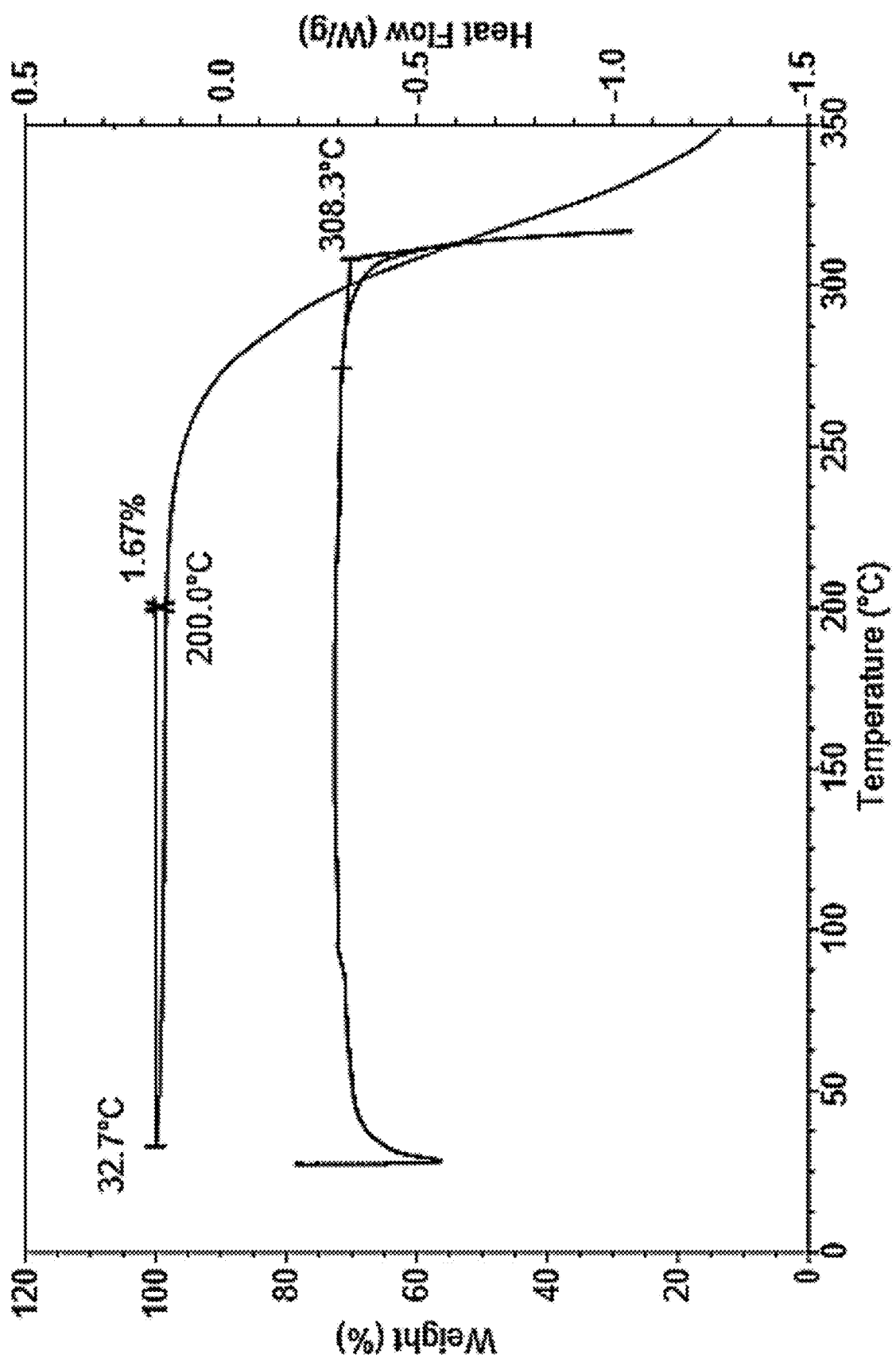
FIG. 3: TGA/DSC curves of the HCl salt type A.

The HCl salt Type A was analyzed by TGA and DSC using the conditions described above with reference to Table 4. As illustrated in FIG. 3, the TGA/DSC data showed a weight loss of 1.7% up to 200° C., and melting (308.3° C., onset temperature) accompanied with decomposition, consistent with the sharp weight loss step in heating.

Ex. 3-3: HPLC Analysis of HCl Salt Type A

Figure 4:
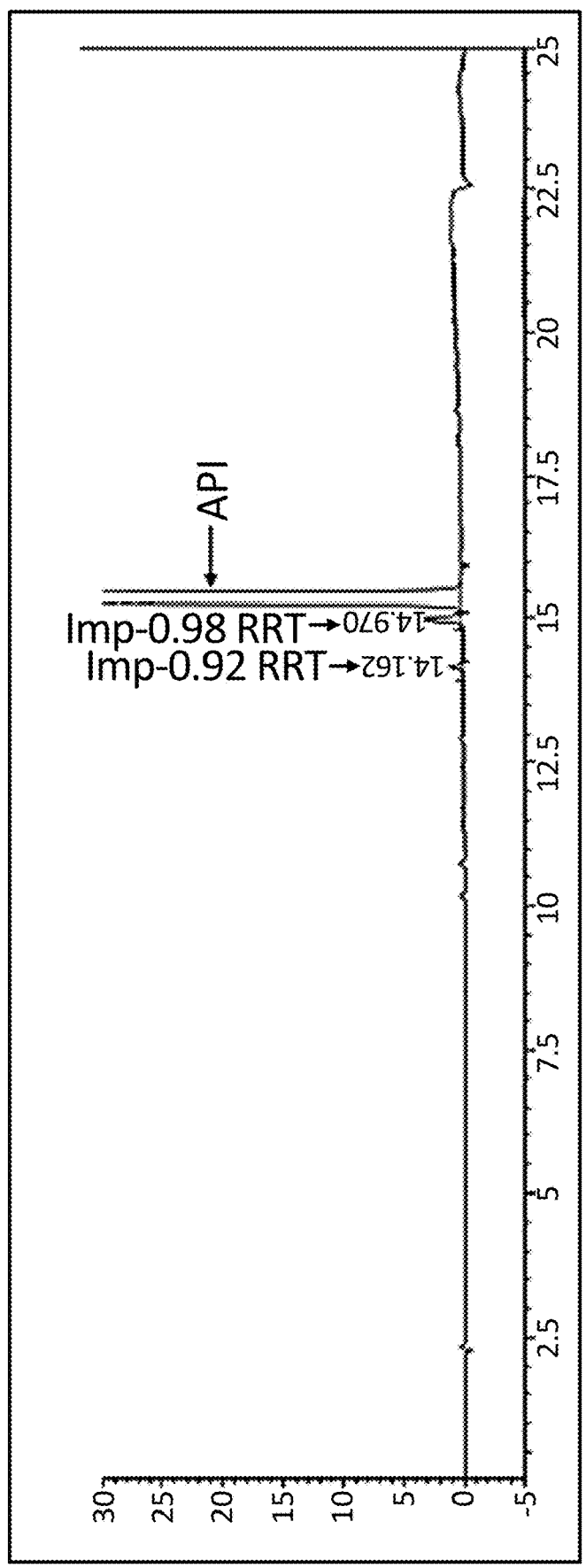
FIG. 4: HPLC chromatogram of HCl salt type A.

The HCl salt Type A of Compound 142 HCl salt was analyzed for purity using the HPLC conditions described above with reference to Table 5. The HPLC purity was determined to be 99.7% (area %). The chromatogram is shown in FIG. 4 and individual impurities were summarized in Table 7.

TABLE 7

Individual impurities of HCl salt Type A

| #Peak | Time (min) | RRT | Area (%) |
|---|---|---|---|
| 1 | 14.15 | 0.92 | 0.09 |
| 2 | 14.98 | 0.98 | 0.25 |
| 3 | 15.35 | 1.00 (API) | 99.66 |

Ex. 3-4: MEC Analysis of HCl Salt Type A

Figure 5:
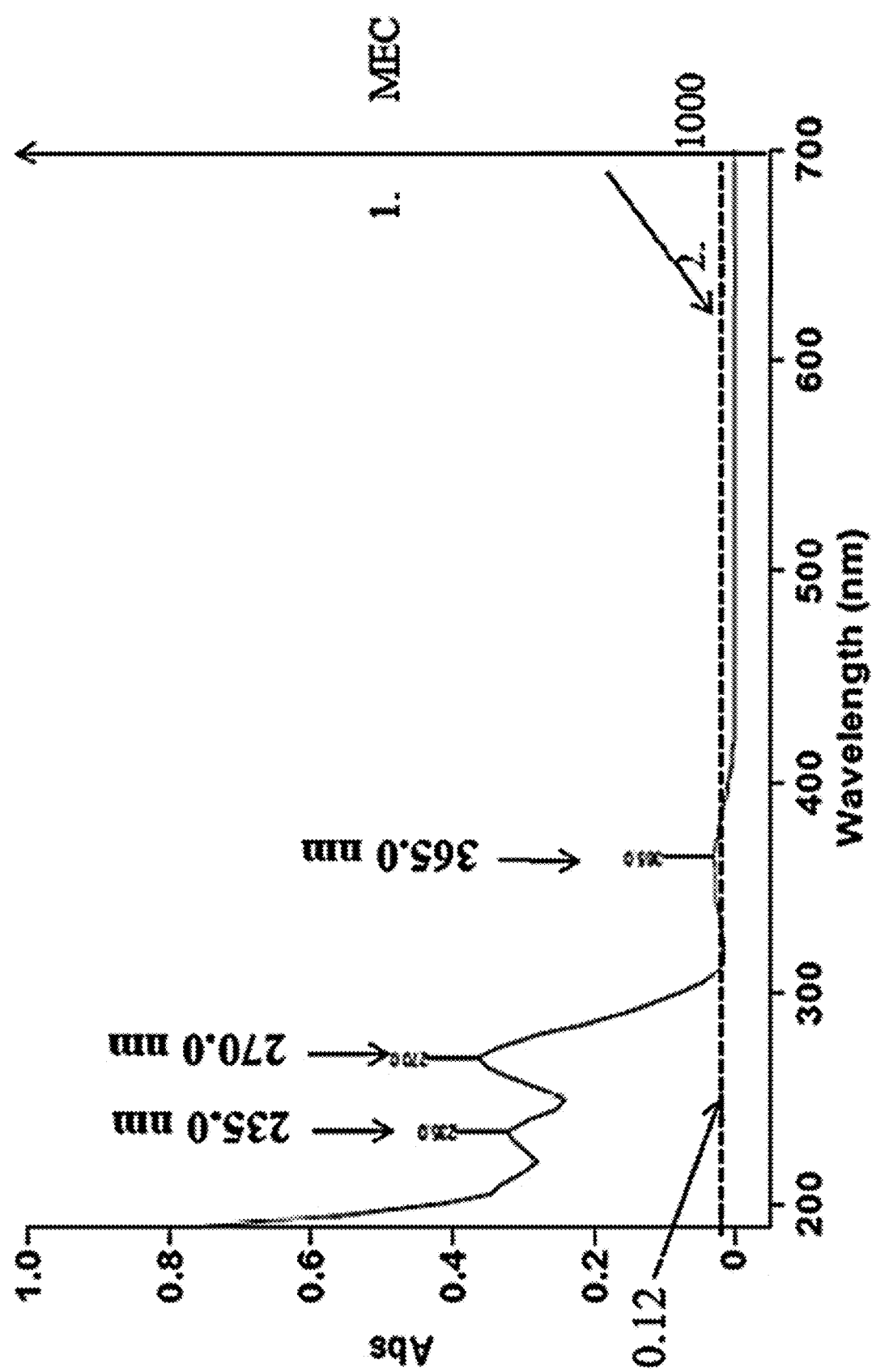
FIG. 5: Full wave scan spectrum of HCl salt type A.

Molar extinction coefficient (MEC) was measured using the conditions described above in order to evaluate the photo reactivity of the HCl salt Type A. Based on the results of full wave scanning (190-700 nm), shown in FIG. 5, 235 nm, 270 nm and 365 nm (absorption maxima) were selected to calculate the MEC. The calculation results in Table 8 showed that the MEC was larger than 1000 L mol−1 cm−1 at all selected wavelength. Based on approximate calculation, the MEC would be large than 1000 L mol−1 cm−1 when absorption is above 0.012 (as shown by the dashed line in FIG. 5).

TABLE 8

Molar absorptivity coefficient calculation table

| Wavelength (nm) | Cell Length (cm) | Conc. (mol/L) | Abs | MEC (L mol$^{-1}$ cm$^{-1}$)* | Ave. |
|---|---|---|---|---|---|
| 235 | 1.0 | 1.22E−05 | 0.3198 | 26246.5 | 26184.9 |
|  |  | 1.22E−05 | 0.3183 | 26123.4 |  |
| 270 | 1.0 | 1.22E−05 | 0.3656 | 30005.4 | 29997.1 |
|  |  | 1.22E−05 | 0.3654 | 29988.9 |  |
| 290** | 1.0 | 1.22E−05 | 0.1659 | 13615.7 | 13591.0 |
|  |  | 1.22E−05 | 0.1653 | 13566.4 |  |
| 365 | 1.0 | 1.22E−05 | 0.0269 | 2207.7 | 2162.6 |
|  |  | 1.22E−05 | 0.0258 | 2117.4 |  |

*Molar extinction (coefficient L mol$^{-1}$ cm$^{-1}$) = Absorbance/conc. (mol/L)/Cell length (cm)
**The wavelength proposed in original request.

Figure 6A:
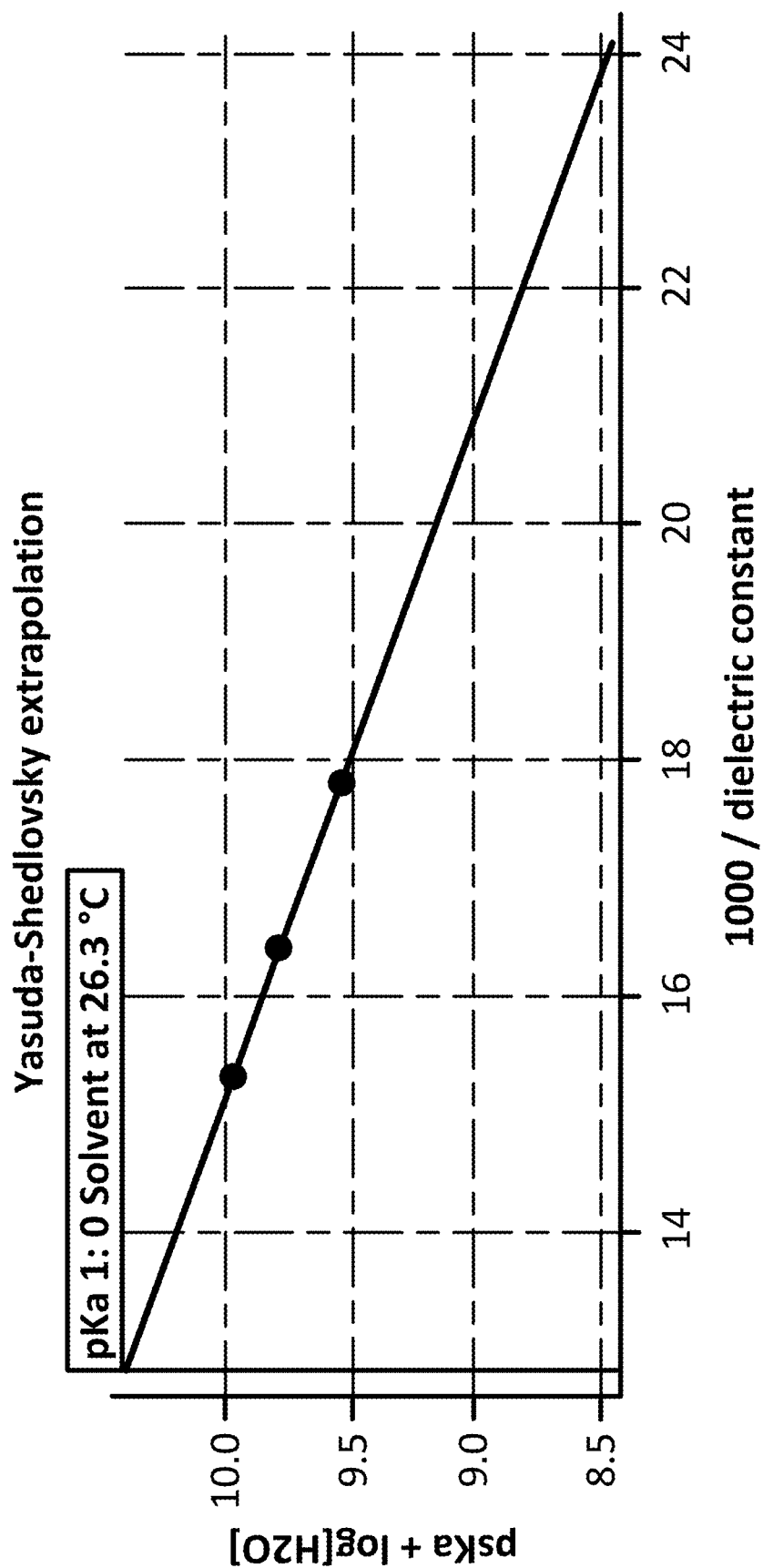
FIG. 6A: Yasuda-Shedlovsky extrapolation curve for pKa measurement of the HCl salt type A.
Figure 6B:
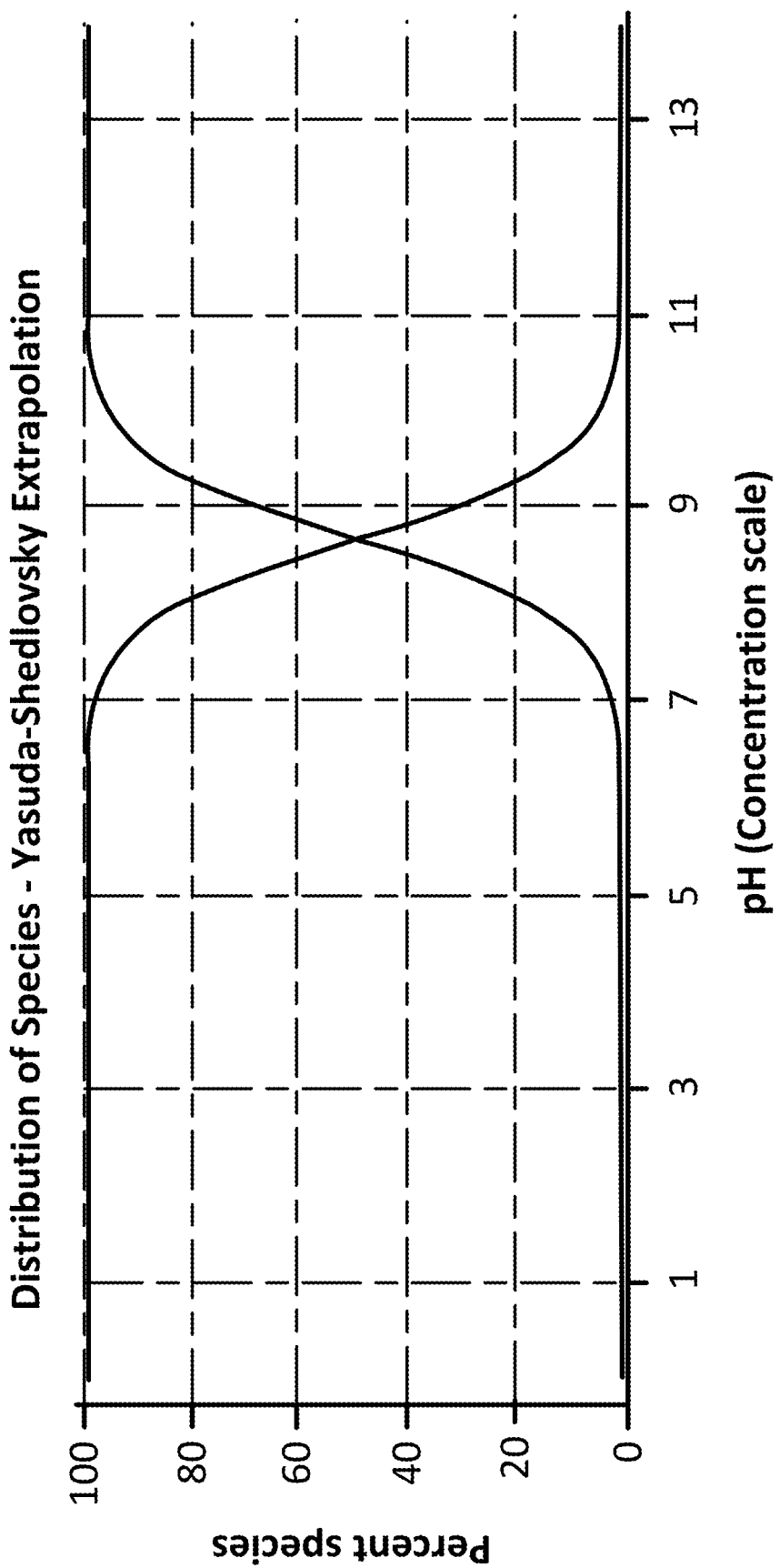
FIG. 6B: Distribution of species—Yasuda-Shedlovsky extrapolation curve for pKa measurement of the HCl salt type A.

Ex. 3-5: pKa Analysis of the HCl Salt Type A pKa of the HCl salt Type A was measured to be 8.68 in MeOH using the conditions describe above, while the simulated value of freebase was 10.45 by Marvin. The extrapolation curves of the pKa measurement are shown in FIGS. 6A and 6B. Table 9 summarizes the pKa data for the HCl salt Type A.

TABLE 9

Summary of pKa data for the HCl salt Type A

| Extrapolation type | SD | Intercept | Slope | R$^2$ | pKa |
|---|---|---|---|---|---|
| Yasuda-Shedlovsky | ±0.01 | 12.66 | −175.0229 | 0.9998 | 8.68 |

Ex. 3-6: Log D7.6 and Log P Analysis of the HCl Salt Type A

Log D7.6 of the HCl salt Type A was tested in pH 7.4 buffer (but the actual pH in final phosphate buffer is 7.6) was performed using the conditions describe above. The measured value of Log D is that of Log D7.6 and was calculated to be 2.87 using the shake-flask method, with the calculation summarized in Table 10. The Log P was calculated as 4.00 using pH as 7.6.

TABLE 10

Data summary for Log $D_{7.6}$ for the HCl salt Type A

| # | Concentration Octanol | (mg/L) pH 7.4 buffer | Fixal pH in phosphate buffer | Log $D_{7.6}$ | Average of Log $D_{7.6}$ | Log P |
|---|---|---|---|---|---|---|
| 1 | 1.31 | 0.0017 | 7.57 | 2.88 | 2.87 | 4.00 |
| 2 | 1.14 | 0.0016 | 7.56 | 2.86 | (RSD-0.34%) | |
| 3 | 1.37 | 0.0018 | 7.56 | 2.87 | | |

Log $D_{7.6}$ = Log (Concentration in octanol/Concentration in pH 7.6 buffer) Log P = Log $D_{7.6}$ + 1 g[1 + $10^{(pKa-pH)}$]

Figure 7:
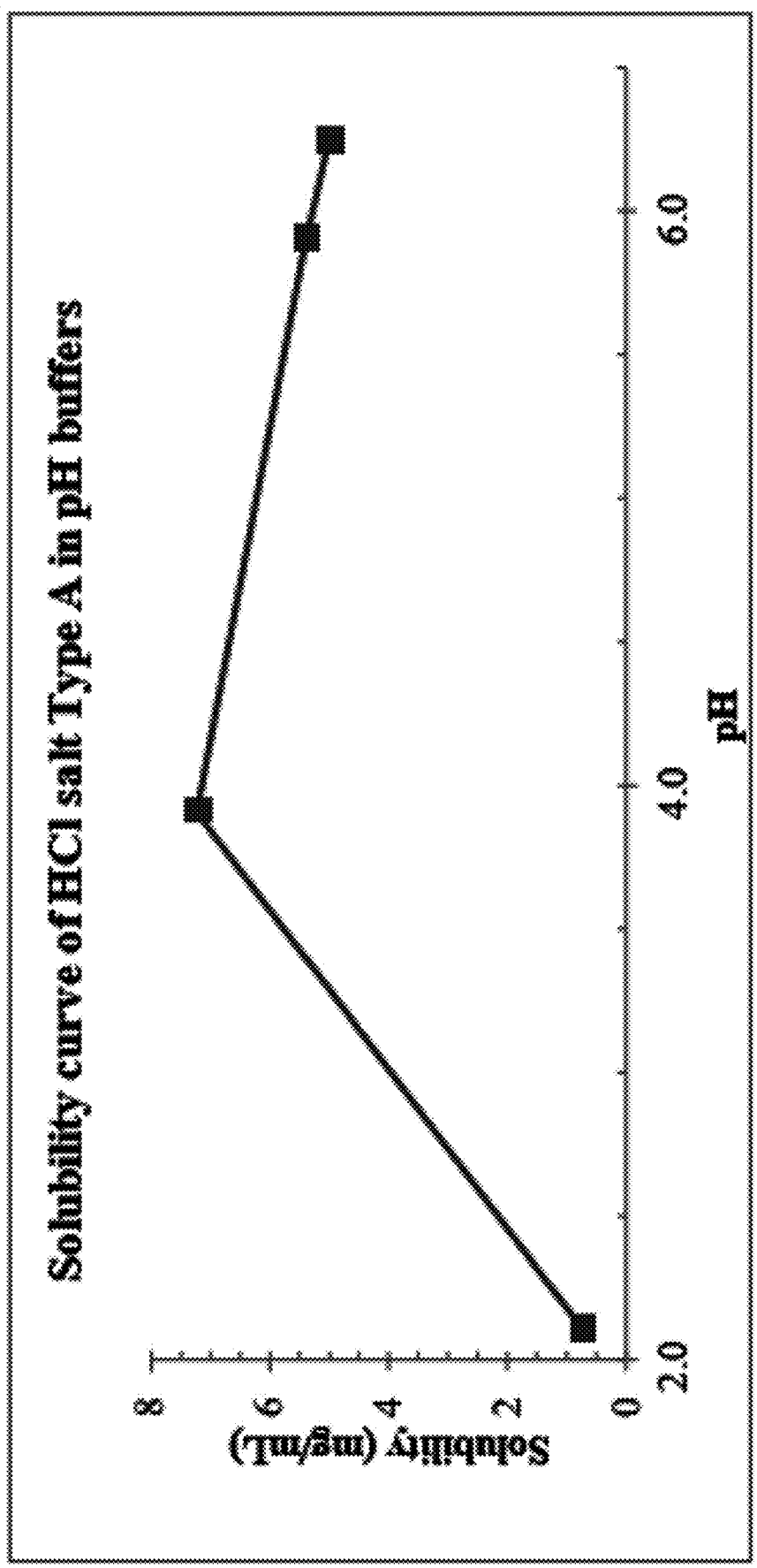
FIG. 7: Solubility curve of the HCl salt type A in pH 2.0-6.0 buffers.
Figure 8:
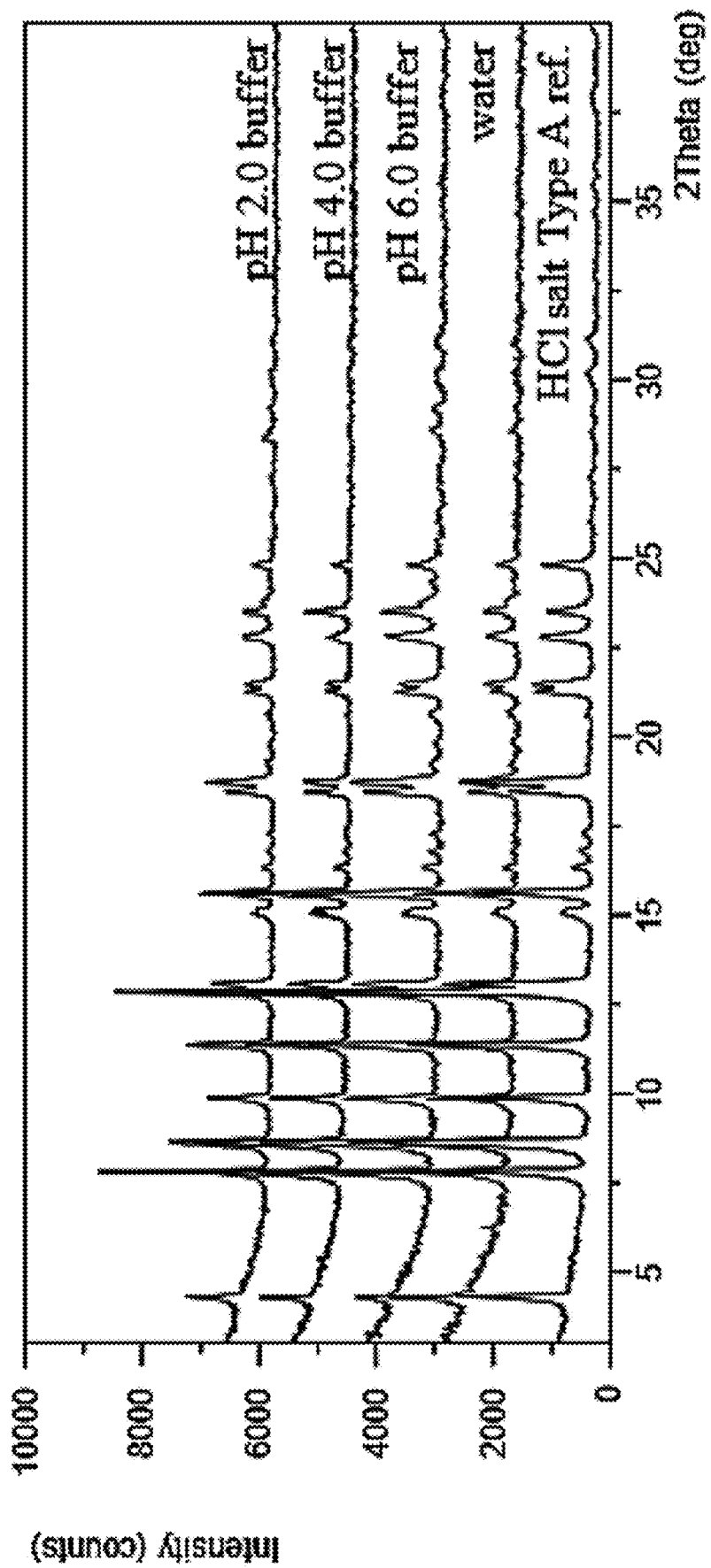
FIG. 8: XRPD overlay of the HCl salt type A in pH 2.0-6.0 buffers, water and as solid form.
Figure 9:
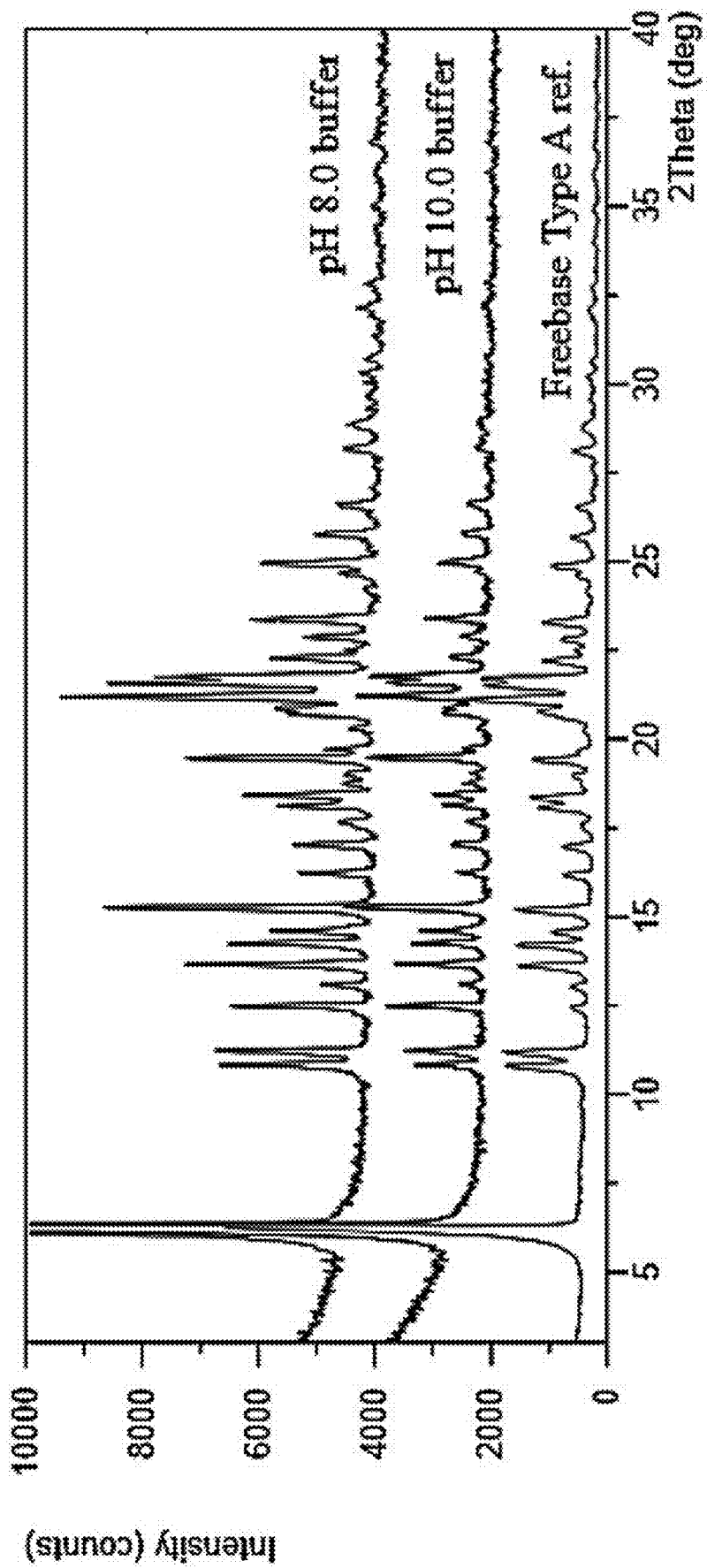
FIG. 9: XRPD overlay of the HCl salt type A in pH 8.0 and 10.0 buffers versus freebase of Compound 142.

Ex. 3-7: Solubility and Stability of the HCl Salt Type A in Different pH Buffers Solubility and stability measurements of the HCl salt type A were conducted in water (native pH of 7.3) and pH buffers (pH 2.0, 4.0, 6.0, 8.0, 10.0) at 25° C. for 24 hours using the conditions described above. The solubility data are summarized in Table 11, and the individual impurities in the supernatant and suspensions are summarized in Tables 12 and 13. FIG. 7 shows the solubility curve of the HCl salt Type A in pH 2.0-6.0 buffers, and the XRPD overlays of the HCl salt Type A in various media and versus the freebase of Compound 142 are shown in FIGS. 8 and 9.

TABLE 11

Solubility of HCl Salt Type A in pH Buffers at 25° C.

| Media | Solubility (mg/mL) | HPLC purity (area %)* Supernatant | HPLC purity (area %)* Suspension | Final pH | Final form of residual solids |
|---|---|---|---|---|---|
| pH 2.0 buffer | 0.73 | 98.8 | 99.7 | 2.1 | HCl salt Type A |
| pH 4.0 buffer | 7.2 | 99.7 | 99.7 | 3.9 | HCl salt Type A |
| pH 6.0 buffer | 5.4 | 99.6 | 99.7 | 5.9 | HCl salt Type A |
| pH 8.0 buffer | 0.20 | 96.5 | 99.7 | 6.9 | Freebase Type A |
| pH 10.0 buffer | 0.0022 | NA | 99.7 | 9.0 | Freebase Type A |
| water (pH = 7.3) | 5.0 | 99.6 | 99.7 | 6.3 | HCl salt Type A |

*The HPLC purity of starting material was 99.7 area %.
NA: not available, due to the low solubility in pH 10.0 buffer.
LOQ = 0.15 μg/mL, LOD = 0.04 μg/mL.

TABLE 12

Summary of individual impurities in supernatant

| | Media | | | | |
|---|---|---|---|---|---|
| RRT | pH 2.0 buffer | pH 4.0 buffer | pH 6.0 buffer | pH 8.0 buffer | water (pH 7.3) |
| 0.33 | <0.03 | <0.05 | <0.05 | 0.08 | <0.05 |
| 0.49 | <0.05 | <0.05 | <0.05 | 0.06 | <0.05 |

TABLE 12-continued

Summary of individual impurities in supernatant

| | Media | | | | |
|---|---|---|---|---|---|
| RRT | pH 2.0 buffer | pH 4.0 buffer | pH 6.0 buffer | pH 8.0 buffer | water (pH 7.3) |
| 0.66 | <0.05 | <0.05 | <0.05 | 0.62 | <0.05 |
| 0.67 | <0.05 | <0.05 | <0.05 | 0.05 | <0.05 |
| 0.70 | 0.31 | <0.05 | 0.06 | 1.37 | 0.07 |
| 0.74 | <0.05 | <0.05 | <0.05 | 0.10 | <0.05 |
| 0.76 | <0.05 | <0.05 | <0.05 | 0.11 | <0.05 |
| 0.81 | 0.05 | <0.05 | <0.05 | 0.13 | <0.05 |
| 0.84 | 0.20 | <0.05 | <0.05 | 0.11 | <0.05 |
| 0.92 | 0.26 | 0.09 | 0.11 | 0.21 | 0.11 |
| 0.93 | <0.05 | <0.05 | <0.05 | 0.08 | <0.05 |
| 0.98 | 0.30 | 0.26 | 0.27 | 0.51 | 0.28 |
| 1.00 (API) | 98.83 | 99.65 | 99.57 | 96.51 | 99.55 |
| 1.05 | 0.06 | <0.05 | <0.05 | 0.09 | <0.05 |

TABLE 13

Summary of individual impurities in suspensions

| | Media | | | | | | |
|---|---|---|---|---|---|---|---|
| RRT | Starting material | pH 2.0 buffer | pH 4.0 buffer | pH 6.0 buffer | pH 8.0 buffer | pH 10.0 buffer | water (pH 7.3) |
| 0.92 | 0.09 | 0.08 | 0.09 | 0.09 | 0.08 | 0.08 | 0.09 |
| 0.98 | 0.25 | 0.26 | 0.25 | 0.26 | 0.26 | 0.26 | 0.26 |
| 1.00 (API) | 99.66 | 99.66 | 99.66 | 99.66 | 99.66 | 99.66 | 99.65 |

HCl salt Type A showed the highest solubility (7.2 mg/mL) in pH 4.0 buffer. No form change was observed in pH 2.0~6.0 buffers and water, while form conversion to freebase of Compound 142 was observed in pH 8.0 and 10.0 buffers. HPLC purity analysis was performed for the suspensions using the conditions described above by reference to Table 5, and the results showed no HPLC purity decrease, indicating that the suspension was stable in all selected pH buffers. The slightly lower purity of supernatant in pH 2.0 and 8.0 buffers may be caused by impurity enrichment in supernatant.

Example 8-8: Solubility Measurement in Organic Solvents

Figure 10:
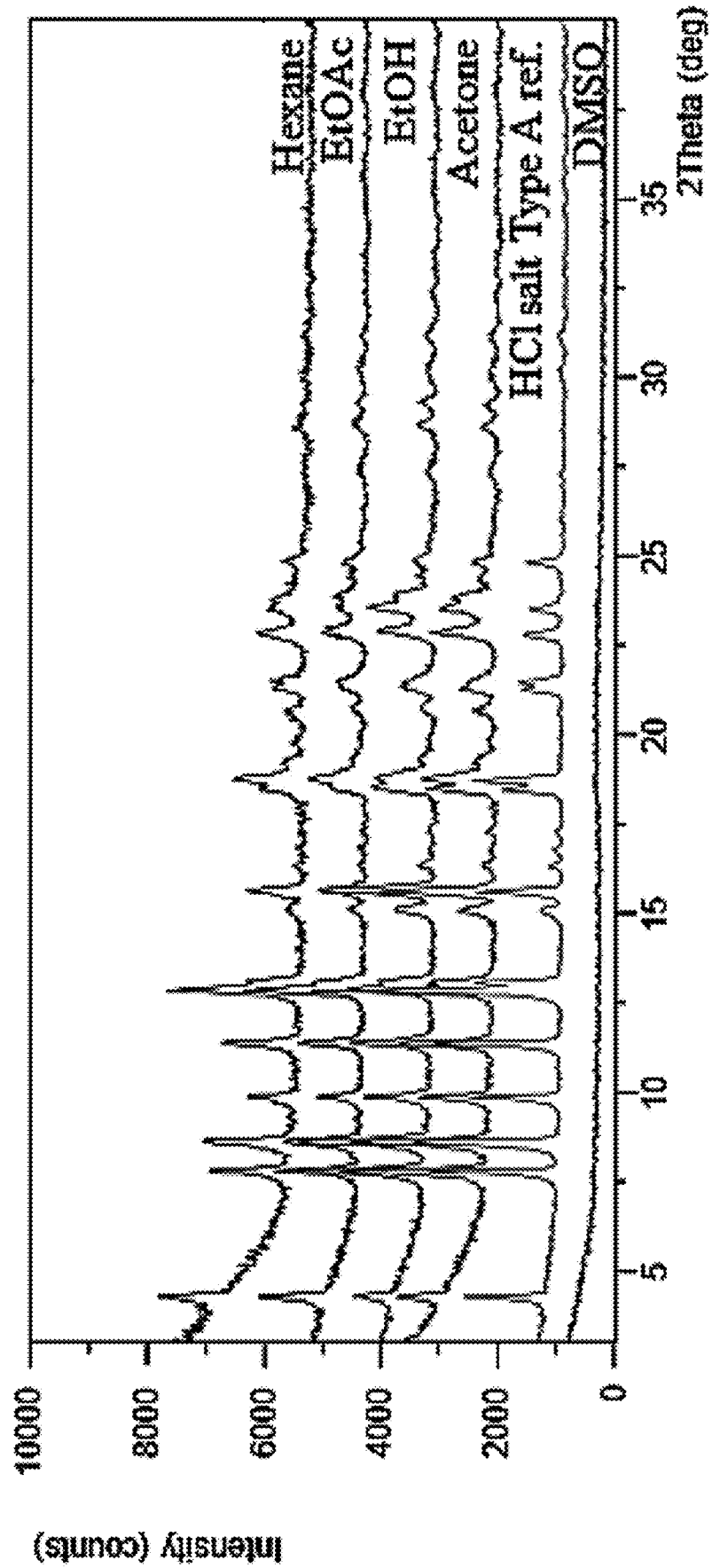
FIG. 10: XRPD overlay of the HCl salt type A in hexane, EtOAc, EtOH, acetone and DMSO.
Figure 11:
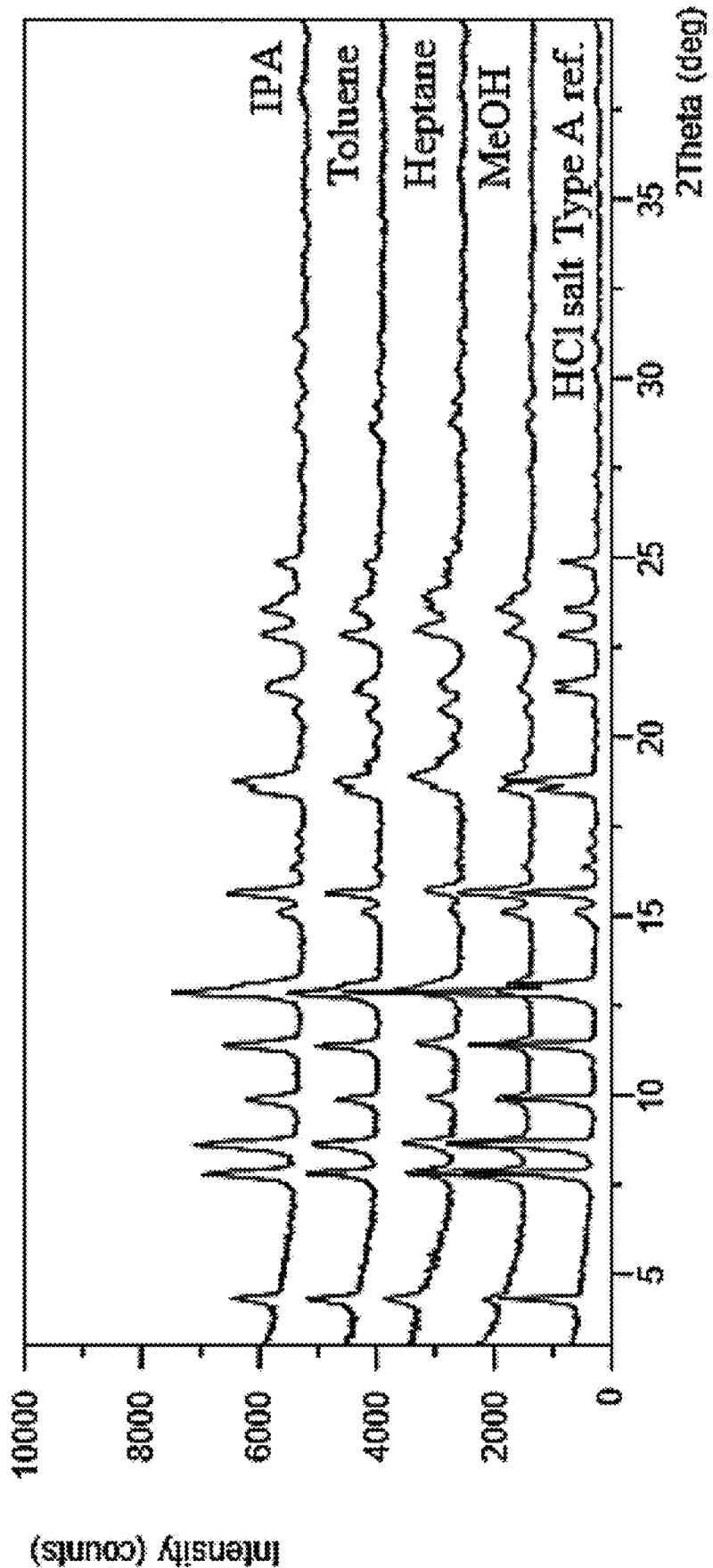
FIG. 11: XRPD overlay of the HCl salt type A in IPA, toluene, heptane and MeOH.

Solubility measurements of the HCl salt Type A were conducted in nine single organic solvents at 25° C. for 24 hours using the procedure described above. The results are summarized in Table 14, and XRPD overlay of residual solids are shown in FIGS. 10 and 11.

TABLE 14

Solubility results for HCl Salt Type A in organic solvents at 25° C.

| Solvent | Solubility (mg/mL) | Final form of residual solids |
|---|---|---|
| DMSO | 33.5 | Amorphons |
| MeOH | 24.9 | HCl salt Type A |
| EtOH | 3.5 | HCl salt Type A |
| IPA | 0.69 | HCl salt Type A |
| Acetone | 0.091 | HCl salt Type A |
| EtQAc | 0.011 | HCl salt Type A |

TABLE 14-continued

Solubility results for HCl Salt Type A in organic solvents at 25° C.

| Solvent | Solubility (mg/mL) | Final form of residual solids |
|---|---|---|
| Toluene | 0.0088 | HCl salt Type A |
| Heptane | 0.0008 | HCl salt Type A |
| Hexane | 0.0004 | HCl salt Type A |

LOQ = 0.15 μg/mL, LOD = 0.04 μg/mL.

The solubility of HCl salt Type A decreased with decreasing solvent polarity. It showed higher solubility (>24.9 mg/mL) in polar solvents (DMSO and MeOH) and lower solubility (<0.088 mg/mL) in nonpolar solvents (hexane, heptane and toluene). Amorphous form of Compound 142 HCl salt was observed in DMSO after 24 hrs, which might be caused by amorphous sample or solvent existence in wet material. No form change was observed in other organic solvents.

Example 4: Preparation of Solid Forms of Compound 142 HCl Salt

Figure 12:
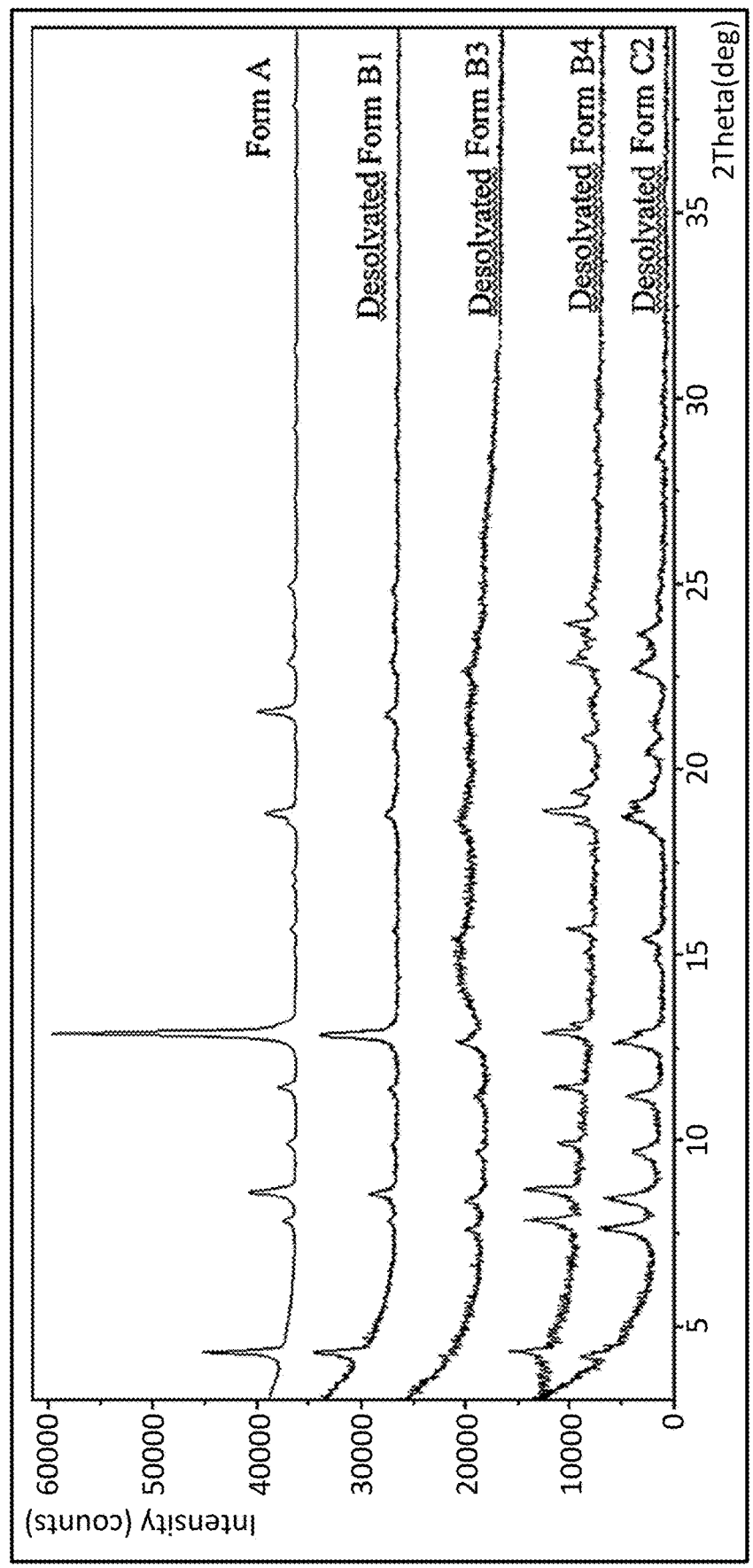
FIG. 12: XRPD overlay of the solid Forms A, B1, B3, B4 and C2 of Compound 142 HCl salt.

The HCl salt Types A, B1, B3, B4 and C2, described in Example 2 by reference to Table 6, were dried at 80° C. to obtain corresponding solid Forms A, BF, B3, B4 and C2 respectively. XRPD analyses were carried out on the solid Forms A, B1, B3, B4 and C2 using the XRPD Method 2 described above by reference to Table 3. For each sample, XRPD analysis was used to assess when solvent removal was complete, such that the solvent-free/de-solvated products exhibited constant (static) XRPD spectra after a sufficient period of drying at 80° C. FIG. 12 shows an XRPD overlay of the solid Forms A, Bi, B3, B4 and C2 of Compound 142 HCl salt. Comparing the XRPD spectra in FIG. 1 versus the XRPD spectra in FIG. 12 shows significant differences between the HCl salt Types A, B1, B3, B4 and C2 and the corresponding solid Forms A, B1, B3, B4 and C2 of Example 4. Table 15 tabulates the XRPD peak data for the solid Forms A, B1, B3, B4 and C2 of Compound 142 HCl salt.

TABLE 15

Tabulated XRPD peak data the solid Forms A, B1, B3, B4 and C2

| Peak | Form A Pos. [°2Th.] | Form B1 (Desolvated) Pos. [°2Th.] | Form B3 (Desolvated) Pos. [°2Th.] | Form B4 (Desolvated) Pos. [°2Th.] | Form C2 (Desolvated) Pos. [°2Th.] |
|---|---|---|---|---|---|
| 1 | 4.295344 | 3.086226 | 3.151474 | 4.325847 | 3.090449 |
| 2 | 7.828126 | 4.325891 | 7.605474 | 7.864596 | 4.211803 |
| 3 | 8.589782 | 7.826012 | 8.382542 | 8.682261 | 7.652018 |
| 4 | 9.932591 | 8.554296 | 9.668267 | 9.922939 | 8.469109 |
| 5 | 11.4306 | 9.898815 | 11.1884 | 11.45475 | 9.704546 |
| 6 | 12.88388 | 11.42543 | 12.643 | 12.90632 | 11.18625 |
| 7 | 13.15762 | 12.81768 | 15.46707 | 13.15015 | 12.62938 |
| 8 | 15.07857 | 12.88396 | 18.60844 | 15.06165 | 14.86658 |
| 9 | 15.67917 | 15.66196 | 20.54866 | 15.70888 | 15.43406 |
| 10 | 16.43526 | 18.76692 | 22.57401 | 18.5501 | 16.19882 |
| 11 | 16.84106 | 20.63375 | 23.55696 | 18.88524 | 18.71832 |
| 12 | 17.20324 | 21.45063 | 24.61394 | 19.40464 | 19.11608 |
| 13 | 18.54813 | 22.85374 | | 19.98103 | 20.41135 |
| 14 | 18.8215 | 23.88219 | | 20.85921 | 21.16774 |
| 15 | 19.39565 | 24.28872 | | 21.80271 | 22.67739 |
| 16 | 20.83549 | 24.81717 | | 22.8908 | 23.63344 |
| 17 | 21.53899 | 28.68214 | | 23.90563 | 24.08545 |
| 18 | 22.81996 | 30.15584 | | 24.44481 | 24.57328 |
| 19 | 23.59596 | 35.66007 | | 24.73779 | 25.26438 |
| 20 | 23.93601 | | | 27.31982 | 28.40659 |
| 21 | 24.91058 | | | 29.19893 | 29.00443 |
| 22 | 25.92364 | | | 35.55556 | 29.93945 |
| 23 | 27.34942 | | | | 35.5132 |
| 24 | 28.36155 | | | | |
| 25 | 29.17986 | | | | |
| 26 | 30.39144 | | | | |
| 27 | 31.2956 | | | | |
| 28 | 33.50499 | | | | |
| 29 | 34.79631 | | | | |
| 30 | 36.08417 | | | | |
| 31 | 37.83448 | | | | |
| 32 | 39.32113 | | | | |

D. Solid Forms of Compound 142 HCl Salt

It was surprisingly discovered that the HCl salt Types A, B1, B2, B3, B4, C1 and C2, described in Example 3 above, contain significant amounts of solvent even after drying at elevated temperature. Further development efforts were undertaken to devise drying methods capable of removing residual solvent without decomposing the HCl salt of Compound 142. As illustrated below, it was found that solvent-free forms of the Compound 142 HCl salt can be formed by drying at 80° C. for periods of time sufficient to yield stable XRPD spectra.

Example 5: Desolvation of Wet/Solvate Forms B1 Compared to Solid Form A

FIG. 13 shows an XRPD overlay of a wet form B1 of Compound 142 HCl salt (i.e., prior to any drying), the solvate form B1 of Compound 142 HCl salt (formed by drying at ambient temperature), the solid form B1 of Compound 142 HCl salt (formed by drying at 80° C.), and the solid Form A of Compound 142 HCl salt (formed by drying at 80°. The XRPD spectra of FIG. 13 were obtain using the XRPD Method 2 described above by reference to Table 3.

The corresponding tabulated peak data for these XRPDs is shown in Table 16. The XRPD peaks of wet form B1 are shifted by about 0.2° relative to the solid Form A of Compound 142 HCl salt.

Notable differences from the solid desolvated Form A peaks as the material is heated, although there still are differences between the desolvated form B1 dried at 80° C. and the solid Form A dried at 80'° C. Thus, the desolvated form B1 of Compound 142 HCl salt is a different solid form than the solid Form A of Compound 142 HCl salt.

TABLE 16

Tabulated XRPD peak data for different stages of Form B1 desolvation in comparison to desolvated Form A of Compound 142 HCl Salt

| Peak | Solid Form A (Dried at 80° C.) Pos. [°2Th.] | Wet Form wB1 (Not Dried) Pos. [°2Th.] | Solvate Form B1 (Ambient Dried) Pos. [°2Th.] | Solid Form B1 (Dried at 80° C.) Pos. [°2Th.] |
|---|---|---|---|---|
| 1 | 4.295344 | 4.140542 | 3.14169 | 3.086226 |
| 2 | 7.828126 | 8.286068 | 4.250688 | 4.325891 |
| 3 | 8.589782 | 11.21555 | 7.776561 | 7.826012 |
| 4 | 9.932591 | 12.45255 | 8.304235 | 8.554296 |
| 5 | 11.4306 | 14.65401 | 8.528115 | 9.898815 |
| 6 | 12.88388 | 15.58902 | 11.28644 | 11.42543 |
| 7 | 13.15762 | 16.7273 | 12.47257 | 12.81768 |
| 8 | 15.07857 | 18.25049 | 12.79233 | 12.88396 |
| 9 | 15.67917 | 20.83231 | 18.74511 | 15.66196 |
| 10 | 16.43526 | 22.15493 | 21.26284 | 18.76692 |
| 11 | 16.84106 | | | 20.63375 |
| 12 | 17.20324 | | | 21.45063 |
| 13 | 18.54813 | | | 22.85374 |
| 14 | 18.8215 | | | 23.88219 |
| 15 | 19.39565 | | | 24.28872 |
| 16 | 20.83549 | | | 24.81717 |
| 17 | 21.53899 | | | 28.68214 |
| 18 | 22.81996 | | | 30.15584 |
| 19 | 23.59596 | | | 35.66007 |
| 20 | 23.93601 | | | |
| 21 | 24.91058 | | | |
| 22 | 25.92364 | | | |
| 23 | 27.34942 | | | |
| 24 | 28.36155 | | | |
| 25 | 29.17986 | | | |
| 26 | 30.39144 | | | |
| 27 | 31.2956 | | | |
| 28 | 33.50499 | | | |
| 29 | 34.79631 | | | |
| 30 | 36.08417 | | | |
| 31 | 37.83448 | | | |
| 32 | 39.32113 | | | |

Example 6: Desolvation of Solvate Form B3 Compared to Solid Form A

Figure 14:
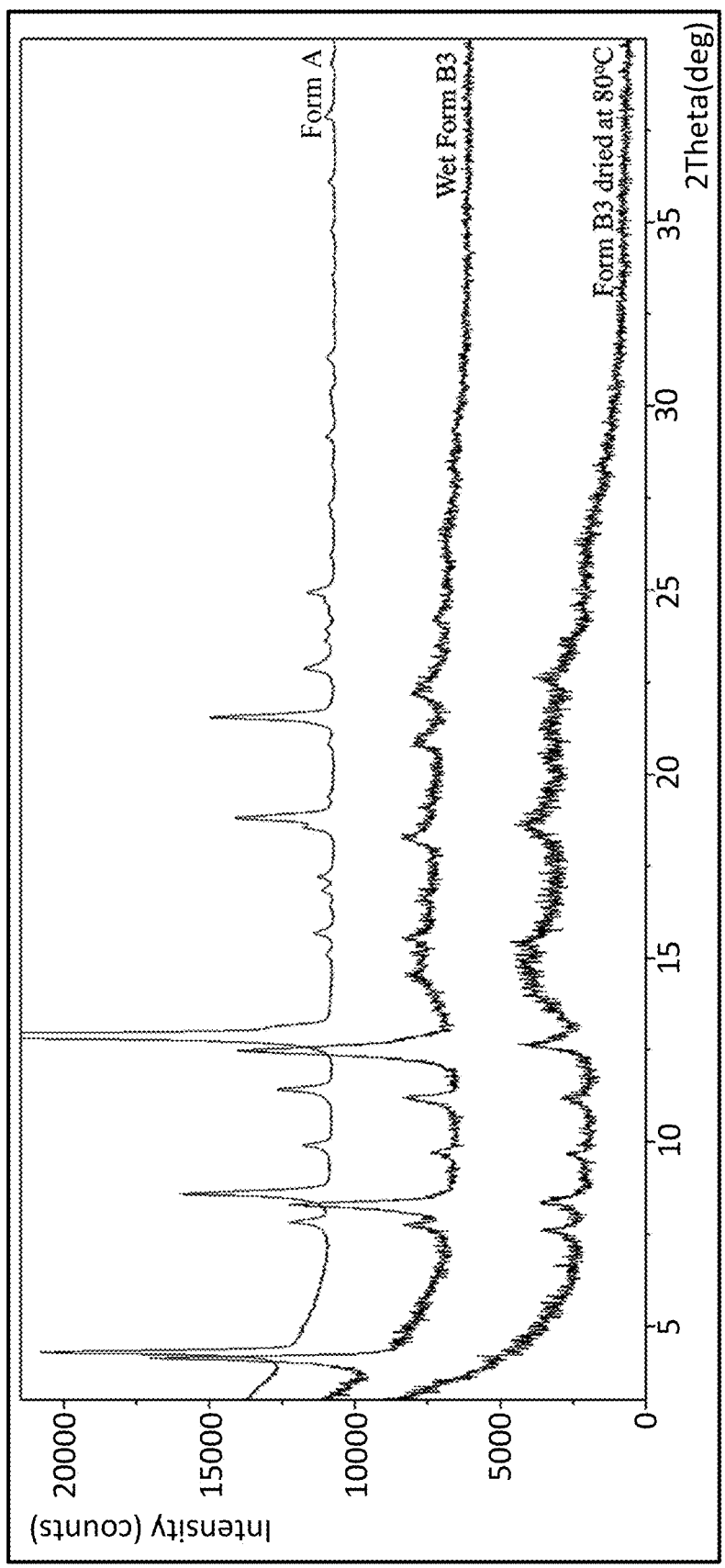
FIG. 14: XRPD overlay of solvated and desolvated forms B3 of Compound 142 HCl salt in comparison to solid Form A of Compound 142 HCl salt.

FIG. 14 shows an XRPD overlay of the solvate form B3 of Compound 142 HCl salt (formed by drying at ambient temperature), the desolvated form B3 of Compound 142 HCl salt (formed by drying at 80° C.), and the solid Form A of Compound 142 HCl salt (formed by drying at 80° C.). The XRPD spectra of FIG. 14 were obtained using the XRPD Method 2 described above by reference to Table 3. The corresponding tabulated peak data for these XRPDs is shown in Table 17. Desolvated form B3 is missing many peaks present in the XRPD of the solid Form A, and the peaks that are present in the desolvated form B3 are similar to the solid Form A but shifted about 0.2°. Notable peak differences from the solid Form A include: 15.54°, 18.25°, and 22.16°. Thus, the desolvated form B3 of Compound 142 HCl salt is a different solid form than the solid Form A of Compound 142 HCl salt.

TABLE 17

Tabulated XRPD peak data for solvate Form B3, desolvated Form B3, and solid Form A of Compound 142 HCl Salt

| Peak | Solid Form A (Dried at 80° C.) Pos. [°2Th.] | Solvate Form B3 (Ambient Dried) Pos. [°2Th.] | Solid Form B3 (Dried at 80° C.) Pos. [°2Th.] |
|---|---|---|---|
| 1 | 4.295344 | 4.131387 | 3.151474 |
| 2 | 7.828126 | 7.774307 | 7.605474 |
| 3 | 8.589782 | 8.311052 | 8.382542 |
| 4 | 9.932591 | 9.752625 | 9.668267 |
| 5 | 11.4306 | 11.22423 | 11.1884 |
| 6 | 12.88388 | 12.48793 | 12.643 |
| 7 | 13.15762 | 14.51984 | 15.46707 |
| 8 | 15.07857 | 15.5478 | 18.60844 |
| 9 | 15.67917 | 18.24626 | 20.54866 |
| 10 | 16.43526 | 20.90721 | 22.57401 |
| 11 | 16.84106 | 22.16186 | 23.55696 |
| 12 | 17.20324 | 24.21946 | 24.61394 |
| 13 | 18.54813 | 26.28546 | |
| 14 | 18.8215 | | |
| 15 | 19.39565 | | |
| 16 | 20.83549 | | |
| 17 | 21.53899 | | |
| 18 | 22.81996 | | |
| 19 | 23.59596 | | |
| 20 | 23.93601 | | |
| 21 | 24.91058 | | |
| 22 | 25.92364 | | |
| 23 | 27.34942 | | |
| 24 | 28.36155 | | |
| 25 | 29.17986 | | |
| 26 | 30.39144 | | |
| 27 | 31.2956 | | |
| 28 | 33.50499 | | |
| 29 | 34.79631 | | |
| 30 | 36.08417 | | |
| 31 | 37.83448 | | |
| 32 | 39.32113 | | |

Example 7: Desolvation of Wet/Solvate Forms B4 Compared to Solid Form A

Figure 15:
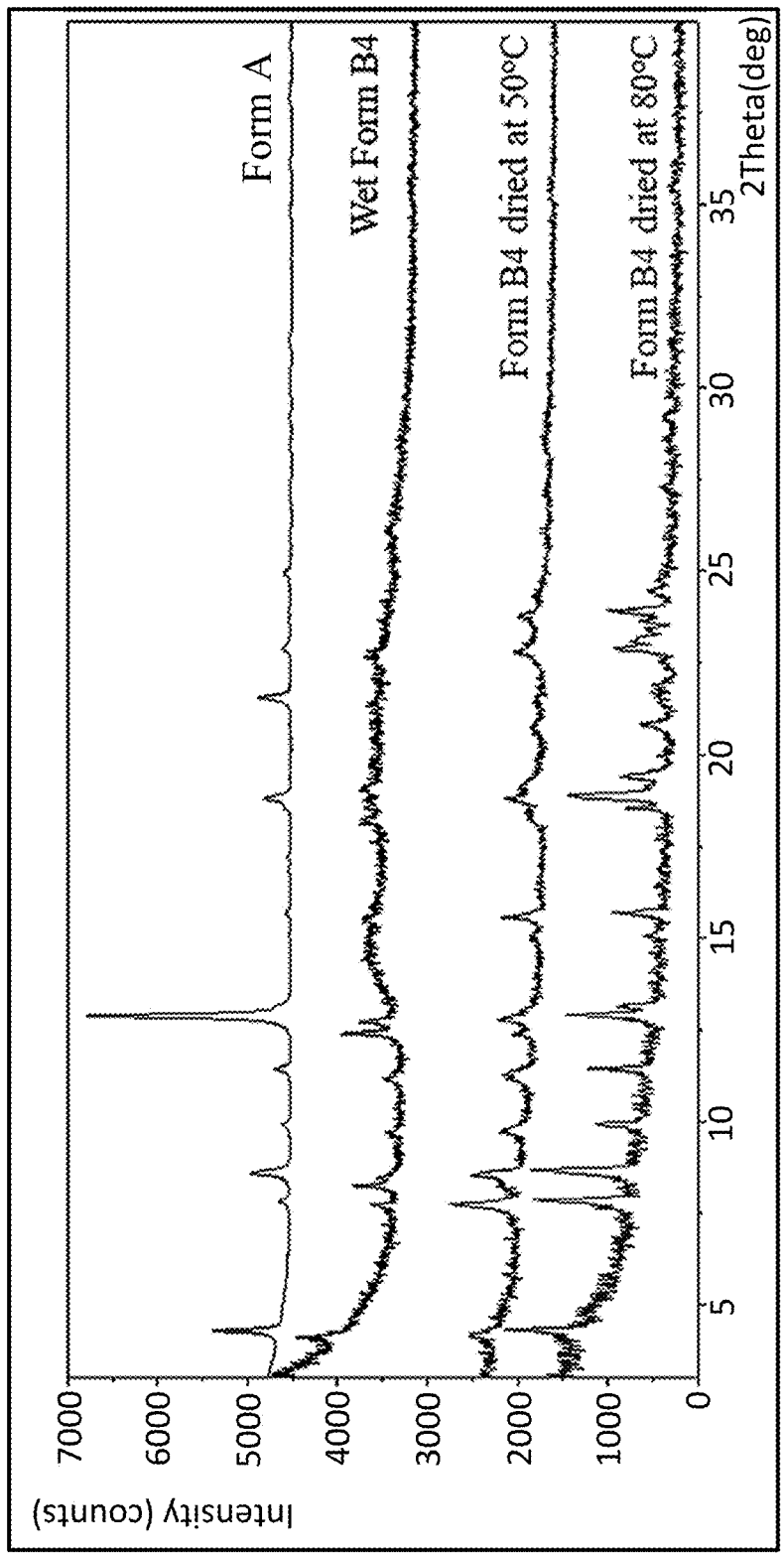
FIG. 15: XRPD overlay of wet, solvated and desolvated forms B4 of Compound 142 HCl salt in comparison to the solid Form A of Compound 142 HCl salt.

FIG. 15 shows an XRPD overlay of a wet form B4 of Compound 142 HCl salt (i.e., prior to any drying), the solvate form B4 of Compound 142 HCl salt (formed by drying at 50° C.), the desolvated form B4 of Compound 142 HCl salt (formed by drying at 80 SC), and the solid Form A of Compound 142 HCl salt (formed by drying at 80° C.). The XRPD spectra of FIG. 15 were obtain using the XRPD Method 2 described above by reference to Table 3. The corresponding tabulated peak data for these XRPDs is shown in Table 18. The XRPD spectrum of the desolvated Form B4 includes some similar peaks to the XRPD spectrum of the solid Form A below 15 degrees. However, the peaks above 15 degrees in the XRPD spectrum of the desolvated Form B4 are marketedly different from the XRPD spectrum of the solid Form A. Thus, the desolvated form B4 of Compound 142 HCl salt is a different solid form than the solid form A of Compound 142 HCl salt.

TABLE 18

Tabulated XRPD peak data for different stages of
Form B4 desolvation in comparison to solid
Form A of Compound 142 HCl Salt

| Peak | Solid Form A (Dried at 80° C.) Pos. [°2Th.] | Wet Form B4 (Not Dried) Pos. [°2Th.] | Solvate Form B4 (Dried at 50° C.) Pos. [°2Th.] | Solid Form B4 (Dried at 80° C.) Pos. [°2Th.] |
|---|---|---|---|---|
| 1 | 4.295344 | 3.138496 | 4.181502 | 4.325847 |
| 2 | 7.828126 | 4.117465 | 7.73936 | 7.864596 |
| 3 | 8.589782 | 7.738936 | 8.582511 | 8.682261 |
| 4 | 9.932591 | 8.241309 | 9.765428 | 9.922939 |
| 5 | 11.4306 | 9.683824 | 11.26657 | 11.45475 |
| 6 | 12.88388 | 11.14028 | 12.37835 | 12.90632 |
| 7 | 13.15762 | 12.38386 | 12.76571 | 13.15015 |
| 8 | 15.07857 | 12.73951 | 15.02099 | 15.06165 |
| 9 | 15.67917 | 15.39651 | 15.55631 | 15.70888 |
| 10 | 16.43526 | 18.18744 | 18.19184 | 18.5501 |
| 11 | 16.84106 | 19.09837 | 18.7918 | 18.88524 |
| 12 | 17.20324 | 22.68827 | 19.0866 | 19.40464 |
| 13 | 18.54813 | 23.67892 | 20.72655 | 19.98103 |
| 14 | 18.8215 | 26.07669 | 21.40399 | 20.85921 |
| 15 | 19.39565 | | 22.75698 | 21.80271 |
| 16 | 20.83549 | | 23.78108 | 22.8908 |
| 17 | 21.53899 | | 24.29057 | 23.90563 |
| 18 | 22.81996 | | 26.03878 | 24.44481 |
| 19 | 23.59596 | | 28.46605 | 24.73779 |
| 20 | 23.93601 | | | 27.31982 |
| 21 | 24.91058 | | | 29.19893 |
| 22 | 25.92364 | | | 35.55556 |
| 23 | 27.34942 | | | |
| 24 | 28.36155 | | | |
| 25 | 29.17986 | | | |
| 26 | 30.39144 | | | |
| 27 | 31.2956 | | | |
| 28 | 33.50499 | | | |
| 29 | 34.79631 | | | |
| 30 | 36.08417 | | | |
| 31 | 37.83448 | | | |
| 32 | 39.32113 | | | |

Example 8: Desolvation of Wet/Solvate Forms C2 Compared to Solid Form A

Figure 16:
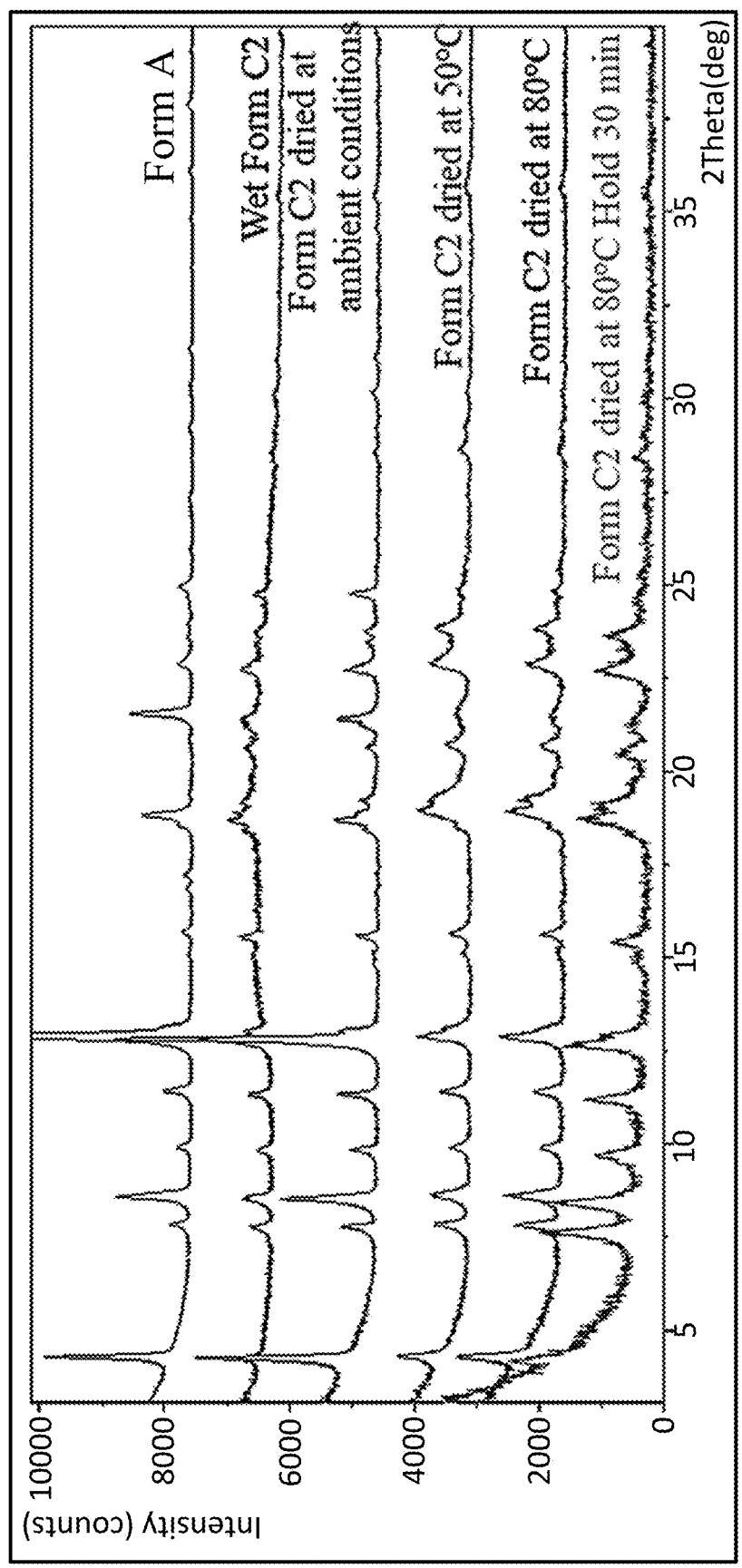
FIG. 16: XRPD overlay of wet, solvated and desolvated forms C2 of Compound 142 HCl salt in comparison to solid Form A of Compound 142 HCl salt.

FIG. 16 shows an XRPD overlay of a wet form C2 of Compound 142 HCl salt (i.e., prior to any drying), a solvate form C2 of Compound 142 HCl salt (formed by drying at ambient temperature), a solvate form C2 of Compound 142 HCl salt (formed by drying at 50° C.), a desolvated form C2 of Compound 142 HCl salt (formed by drying at 80° C.), a desolvated form C2 of Compound 142 HCl salt (formed by drying at 80° C., held at 80° C. for 30 min), and the solid Form A of Compound 142 HCl salt (formed by drying at 80° C.). The XRPD spectra of FIG. 16 were obtain using the XRPD Method 2 described above by reference to Table 3. The corresponding tabulated peak data for these XRPDs is shown in Table 19. The XRPD spectrum of the wet Form C2 includes significant differences compared to the XRPD spectrum of the solid Form A-including the presence of peaks at 19.81°, 20.600 and 21.15° in the XPRD of the wet Form C2. These peaks decrease in intensity as the solvated Form C2 is desolvated to form the desolvated Form C2. It is clear from the respective XRPD spectra that the desolvated form C2 of Compound 142 HCl salt is a different solid form than the solid Form A of Compound 142 HCl salt.

TABLE 19

Tabulated XRPD peak data for different stages of Form C2 desolvation in comparison
to desolvated Form A of Compound 142 HCl Salt

| Peak | Solid Form A (Dried 80° C.) Pos. [°2Th.] | Wet Form C2 (Not Dried) Pos. [°2Th.] | Solvate Form C2 (Air Dried) Pos. [°2Th.] | Solvate Form C2 (Dried at 50° C.) Pos. [°2Th.] | Solid Form C2 (Dried at 80° C.) Pos. [°2Th.] | Solid Form C2 (Dried 80° C.) (hold 30 min) |
|---|---|---|---|---|---|---|
| 1 | 4.295344 | 4.271144 | 4.28079 | 4.302839 | 4.316704 | 3.090449 |
| 2 | 7.828126 | 7.786222 | 7.824115 | 7.844005 | 7.817598 | 4.211803 |
| 3 | 8.589782 | 8.571107 | 8.531546 | 8.674357 | 8.627967 | 7.652018 |
| 4 | 9.932591 | 9.8279 | 9.856264 | 9.911423 | 9.908219 | 8.469109 |
| 5 | 11.4306 | 11.3655 | 11.37463 | 11.42691 | 11.41016 | 9.704546 |
| 6 | 12.88388 | 12.78576 | 12.81617 | 12.85468 | 12.86462 | 11.18625 |
| 7 | 13.15762 | 13.03702 | 13.05317 | 13.11697 | 15.19582 | 12.62938 |
| 8 | 15.07857 | 15.06054 | 14.85728 | 15.13912 | 15.61867 | 14.86658 |
| 9 | 15.67917 | 15.54895 | 15.11328 | 15.65038 | 16.32077 | 15.43406 |
| 10 | 16.43526 | 16.32077 | 15.58767 | 16.40208 | 18.47731 | 16.19882 |
| 11 | 16.84106 | 18.37376 | 18.41896 | 18.55668 | 18.94184 | 18.71832 |
| 12 | 17.20324 | 18.6743 | 18.69408 | 18.95844 | 19.27091 | 19.11608 |
| 13 | 18.54813 | 19.20712 | 19.20151 | 19.28626 | 19.89822 | 20.41135 |
| 14 | 18.8215 | 19.81691 | 20.66276 | 19.85756 | 20.66151 | 21.16774 |
| 15 | 19.39565 | 20.60807 | 21.1991 | 20.74948 | 21.4223 | 22.67739 |
| 16 | 20.83549 | 21.15845 | 21.43993 | 21.56394 | 22.83314 | 23.63344 |
| 17 | 21.53899 | 21.4219 | 22.70474 | 22.78057 | 23.43501 | 24.08545 |
| 18 | 22.81996 | 22.69875 | 23.46887 | 23.47566 | 23.82175 | 24.57328 |
| 19 | 23.59596 | 23.43501 | 23.75207 | 23.77884 | 24.41067 | 25.26438 |
| 20 | 23.93601 | 23.72701 | 24.77715 | 24.41067 | 24.84586 | 28.40659 |
| 21 | 24.91058 | 24.73236 | 28.5692 | 24.86463 | 25.46223 | 29.00443 |
| 22 | 25.92364 | 25.34569 | 29.13623 | 25.5083 | 28.56758 | 29.93945 |
| 23 | 27.34942 | 28.49408 | 30.15557 | 27.54368 | 29.16705 | 35.5132 |
| 24 | 28.36155 | 30.10794 | 31.09278 | 28.62928 | 30.14089 | |
| 25 | 29.17986 | 31.00648 | 34.55313 | 29.26912 | 35.61159 | |
| 26 | 30.39144 | 32.86645 | 35.40754 | 30.27415 | | |
| 27 | 31.2956 | 34.53321 | 37.97327 | 35.6581 | | |

TABLE 19-continued

Tabulated XRPD peak data for different stages of Form C2 desolvation in comparison to desolvated Form A of Compound 142 HCl Salt

| Peak | Solid Form A (Dried 80° C.) Pos. [°2Th.] | Wet Form C2 (Not Dried) Pos. [°2Th.] | Solvate Form C2 (Air Dried) Pos. [°2Th.] | Solvate Form C2 (Dried at 50° C.) Pos. [°2Th.] | Solid Form C2 (Dried at 80° C.) Pos. [°2Th.] | Solid Form C2 (Dried 80° C.) (hold 30 min) |
|---|---|---|---|---|---|---|
| 28 | 33.50499 | 35.46226 | 39.06947 | 38.00497 | | |
| 29 | 34.79631 | | | | | |
| 30 | 36.08417 | | | | | |
| 31 | 37.83448 | | | | | |
| 32 | 39.32113 | | | | | |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety.

We claim:

1. A solid Form A of 1-(6-ethyl-8-fluoro-4-methyl-3-(3-methyl-1,2,4-oxadiazol-5-yl)quinolin-2-yl)-N-(tetrahydro-2H-pyran-4-yl)piperidin-4-amine hydrochloride exhibiting at least X-ray lines (in degrees 2θ±0.2) at 4.30, 8.59, 12.88, 18.82 and 21.34 in a powder diffraction pattern when measured using Cu Kα radiation.

2. The solid Form A of claim 1, wherein the powder diffraction pattern exhibits at least X-ray lines (in degrees 2θ±0.2) at 4.30, 8.59, 12.88, 18.82 and 21.34, and at least one X-ray line (in degrees 2θ±0.2) selected from the group consisting of 7.83, 9.93, 11.43, 18.55, 22.82 and 29.92.

3. The solid Form A of claim 1, wherein the powder diffraction pattern exhibits at least X-ray lines (in degrees 2θ±0.2) at 4.30, 8.59, 12.88, 18.82 and 21.34, and at least two X-ray lines (in degrees 2θ±0.2) selected from the group consisting of 7.83, 9.93, 11.43, 18.55, 22.82 and 29.92.

4. The solid Form A of claim 1, wherein the powder diffraction pattern exhibits at least X-ray lines (in degrees 2θ±0.2) at 4.30, 7.83, 8.59, 9.93, 11.43, 12.88, 18.82, 18.55, 21.34, 22.82 and 29.92.

5. The solid Form A of claim 1, wherein the powder diffraction pattern exhibits at least X-ray lines (in degrees 2θ±0.2) at 4.30, 7.83, 8.59, 9.93, 11.43, 12.88, 18.82, 18.55, 21.34, 22.82 and 29.92, and at least one X-ray line (in degrees 2θ±0.2) selected from the group consisting of 13.16, 15.08, 15.68, 16.44, 16.84, 17.20, 19.40, 20.84, 23.60, 23.94, 24.91, 27.35, 28.36, 29.18, 30.39, 31.30, 33.50, 34.80, 36.08, 37.83 and 39.32.

6. The solid Form A of claim 1, wherein the powder diffraction pattern exhibits at least X-ray lines (in degrees 2θ±0.2) at 4.30, 7.83, 8.59, 9.93, 11.43, 12.88, 18.82, 18.55, 21.34, 22.82 and 29.92, and at least two X-ray lines (in degrees 2θ±0.2) selected from the group consisting of 13.16, 15.08, 15.68, 16.44, 16.84, 17.20, 19.40, 20.84, 23.60, 23.94, 24.91, 27.35, 28.36, 29.18, 30.39, 31.30, 33.50, 34.80, 36.08, 37.83 and 39.32.

7. The solid Form A of claim 1, wherein the powder diffraction pattern exhibits at least X-ray lines (in degrees 2θ±0.2) at 4.30, 7.83, 8.59, 9.93, 11.43, 12.88, 18.82, 18.55, 21.34, 22.82 and 29.92, and at least three X-ray lines (in degrees 2θ±0.2) selected from the group consisting of 13.16, 15.08, 15.68, 16.44, 16.84, 17.20, 19.40, 20.84, 23.60, 23.94, 24.91, 27.35, 28.36, 29.18, 30.39, 31.30, 33.50, 34.80, 36.08, 37.83 and 39.32.

8. The solid Form A of claim 1, wherein the powder diffraction pattern exhibits at least X-ray lines (in degrees 2θ±0.2) at 4.30, 7.83, 8.59, 9.93, 11.43, 12.88, 13.16, 15.08, 15.68, 16.44, 16.84, 17.20, 18.82, 18.55, 19.40, 20.84, 21.34, 22.82, 23.60, 23.94, 24.91, 27.35, 28.36, 29.18, 29.92, 30.39, 31.30, 33.50, 34.80, 36.08, 37.83 and 39.32.

9. The solid Form A of claim 1, wherein the powder diffraction pattern exhibits at least X-ray lines at the same angles (in degrees 2θ±0.2) in the Table 1.

10. The solid Form A of claim 9, wherein the powder diffraction pattern is substantially free of additional X-ray lines not included in Table 1.

11. The solid Form A of claim 1, wherein the powder diffraction pattern exhibits an X-ray pattern essentially the same as that provided in FIG. 13.

12. The solid Form A of claim 1, wherein the powder diffraction pattern is substantially free of X-ray lines (in degrees 2θ±0.2) at 3.1, 19.1, 20.0, 20.5, 21.2, 24.3, 25.3, 29.9 and 35.5.

13. The solid Form A of claim 1, wherein the powder diffraction pattern is substantially free of X-ray lines (in degrees 2θ±0.2) at 3.1, 9.7, 11.2, 12.6, 15.4, 16.2, 19.1, 20.0, 20.5, 21.2, 21.8, 24.3, 24.6, 25.3, 29.9 and 35.5.

14. A composition comprising the solid Form A of claim 1 and a pharmaceutically acceptable carrier, diluent or excipient.

15. A method for antagonizing the KOR, the method comprising contacting the KOR with an effective amount of the solid Form A of claim 1, or a composition comprising the same.

16. A method for reducing serum prolactin levels, the method comprising administering to a subject in need thereof an effective amount of the solid Form A of claim 1, or a pharmaceutical composition comprising the same, at a frequency and for duration sufficient to provide a beneficial effect to the subject.

17. A method for treating a neuropsychiatric or behavioral condition, whether organic, stress-induced or iatrogenic, that is characterized by elevations in serum prolactin, the method comprising administering to a subject in need thereof an effective amount of the solid Form A of claim 1, or a pharmaceutical composition comprising the same, at a frequency and for a duration sufficient to provide a beneficial effect to the subject.

18. A method for treating a of disorders related to substance abuse or addiction, the method comprising administering to a subject in need thereof an effective amount of the solid Form A of claim 1, or a pharmaceutical composition comprising the same, at a frequency and for a duration sufficient to provide a beneficial effect to the subject.

19. A method treating a CNS-related disorder, the method comprising administering to a subject in need thereof an effective amount of the solid Form A of claim 1, or a pharmaceutical composition comprising the same, at a frequency and for a duration sufficient to provide a beneficial effect to the subject.

20. A method for treating an anxiety disorder, the method comprising administering to a subject in need thereof an effective amount of the solid Form A of claim 1, or a pharmaceutical composition comprising the same, at a frequency and for duration sufficient to provide a beneficial effect to the subject.

21. The method of claim 20, wherein the anxiety disorder is PTSD or GAD.

22. A method for treating a depressive disorder, the method comprising administering to a subject in need thereof an effective amount of the solid Form A of claim 1, or a pharmaceutical composition comprising the same, at a frequency and for duration sufficient to provide a beneficial effect to the subject.

23. The method of claim 22, wherein the depressive disorder is major depression.

24. A method for treating a mood disorder, the comprising administering to a subject in need thereof the solid Form A of claim 1, or a pharmaceutical composition comprising the same, at a frequency and for duration sufficient to provide a beneficial effect to the subject.

25. The method of claim 24, wherein the mood disorder is anhedonia or major depression.

26. A method for treating a schizophrenia or a schizoaffective disorder, the method comprising administering to a subject in need thereof an effective amount of the solid Form A of claim 1, or a pharmaceutical composition comprising the same, at a frequency and for duration sufficient to provide a beneficial effect to the subject.

27. A method for treating obesity or an eating disorder, the method comprising administering to a subject in need thereof an effective amount of the solid Form A of claim 1, or a pharmaceutical composition comprising the same, at a frequency and for duration sufficient to provide a beneficial effect to the subject.

28. A method for treating migraine, the method comprising administering to a subject in need thereof an effective amount of the solid Form A of claim 1, or a pharmaceutical composition comprising the same, at a frequency and for duration sufficient to provide a beneficial effect to the subject.

29. The method of claim 28, wherein the method for treating migraine is for migraine prophylaxis.

30. A method for treating postnatal depression, the method comprising administering to a subject in need thereof an effective amount of the solid Form A of claim 1, or a pharmaceutical composition comprising the same, at a frequency and for duration sufficient to provide a beneficial effect to the subject.

* * * * *